(12) United States Patent
Gerry et al.

(10) Patent No.: US 7,431,728 B2
(45) Date of Patent: Oct. 7, 2008

(54) ULTRASOUND MEDICAL DEVICES, SYSTEMS AND METHODS

(75) Inventors: Jason Gerry, Woburn, MA (US); Charles Vadala, Jr., Boston, MA (US); Bernard Alford, Malden, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 120 days.

(21) Appl. No.: 11/515,545

(22) Filed: Sep. 5, 2006

(65) Prior Publication Data

US 2007/0085611 A1    Apr. 19, 2007

Related U.S. Application Data

(60) Provisional application No. 60/714,456, filed on Sep. 6, 2005.

(51) Int. Cl.
*A61B 8/00* (2006.01)
*H03L 7/00* (2006.01)

(52) U.S. Cl. ............... 606/169; 331/16; 331/4

(58) Field of Classification Search ........... 604/22; 606/128, 169; 331/34, 16, 17, 4
See application file for complete search history.

(56) References Cited

U.S. PATENT DOCUMENTS

| | | | |
|---|---|---|---|
| 2,917,691 A | 12/1959 | De Prisco et al. |
| 3,432,691 A | 3/1969 | Shoh |
| 3,443,610 A | 5/1969 | Eriksson et al. |
| 3,980,906 A | 9/1976 | Kuris et al. |
| 3,990,452 A | 11/1976 | Murry et al. |
| 4,063,557 A | 12/1977 | Wuchinich et al. |
| 4,223,676 A | 9/1980 | Wuchinich et al. |
| 4,587,958 A | 5/1986 | Noguchi et al. |
| 4,708,127 A | 11/1987 | Abdelghani |
| 4,750,488 A | 6/1988 | Wuchinich et al. |
| 4,750,902 A | 6/1988 | Wuchinich et al. |

(Continued)

FOREIGN PATENT DOCUMENTS

EP    0261810    3/1988

(Continued)

OTHER PUBLICATIONS

International Search Report and Written Opinion; PCT/US2006/034449; mailed Apr. 18, 2007.

(Continued)

*Primary Examiner*—Joseph Chang
(74) *Attorney, Agent, or Firm*—Fish & Richardson P.C.

(57) ABSTRACT

Ultrasound medical devices, systems and methods are described. According to an example method, an absolute value of a first input to a voltage controlled oscillator (VCO) is determined. The VCO is in electrical communication with an acoustic assembly of an ultrasound medical device. If the absolute value of the first input to the VCO is in a first range, a second input to the VCO is maintained. If the absolute value of the first input to the VCO is in a second range, the second input to the VCO is adjusted by a first voltage. If the absolute value of the first input to the VCO is in a third range, the second input to the VCO is adjusted by a second voltage.

20 Claims, 34 Drawing Sheets

U.S. PATENT DOCUMENTS

| | | |
|---|---|---|
| 4,808,948 A | 2/1989 | Patel et al. |
| 4,870,953 A | 10/1989 | DonMicheal et al. |
| 4,961,424 A | 10/1990 | Kubota et al. |
| 4,965,532 A | 10/1990 | Sakurai |
| 5,001,649 A | 3/1991 | Lo et al. |
| 5,003,965 A | 4/1991 | Talish et al. |
| 5,062,827 A | 11/1991 | Wiksell |
| 5,076,276 A | 12/1991 | Sakurai et al. |
| 5,116,343 A | 5/1992 | Ams et al. |
| 5,334,183 A | 8/1994 | Wuchinich |
| 5,344,395 A | 9/1994 | Whalen et al. |
| 5,357,423 A | 10/1994 | Weaver et al. |
| 5,447,509 A | 9/1995 | Mills et al. |
| 5,582,588 A | 12/1996 | Sakurai et al. |
| 5,594,375 A | 1/1997 | Carlson et al. |
| 5,673,041 A | 9/1997 | Chatigny et al. |
| 5,776,065 A | 7/1998 | Mehmanpazir et al. |
| 5,830,127 A | 11/1998 | DeCastro |
| 5,897,569 A | 4/1999 | Kellogg et al. |
| 5,968,007 A | 10/1999 | Simon et al. |
| 6,083,191 A | 7/2000 | Rose |
| 6,113,558 A | 9/2000 | Rosenschein et al. |
| 6,551,337 B1 | 4/2003 | Rabiner et al. |
| 6,577,042 B2 | 6/2003 | Lee et al. |
| 6,611,793 B1 | 8/2003 | Burnside et al. |
| 6,679,873 B2 | 1/2004 | Rabiner et al. |
| 6,689,087 B2 | 2/2004 | Pal et al. |
| 6,695,782 B2 | 2/2004 | Ranucci et al. |
| 6,730,048 B1 | 5/2004 | Hare et al. |
| 6,733,451 B2 | 5/2004 | Rabiner et al. |
| 6,802,835 B2 | 10/2004 | Rabiner et al. |
| 2001/0039389 A1 | 11/2001 | Sakurai et al. |
| 2003/0028287 A1 | 2/2003 | Puskas |
| 2003/0045887 A1 | 3/2003 | Sakurai et al. |
| 2003/0065263 A1 | 4/2003 | Hare et al. |
| 2004/0039375 A1 | 2/2004 | Miyazawa |
| 2004/0204729 A1 | 10/2004 | Cimino |
| 2004/0236291 A1 | 11/2004 | Zelickson et al. |
| 2006/0116610 A1 | 6/2006 | Hare et al. |

FOREIGN PATENT DOCUMENTS

| | | |
|---|---|---|
| EP | 1201196 A1 | 5/2002 |
| EP | 1535583 A1 | 6/2005 |
| WO | WO 98/53508 | 11/1998 |
| WO | WO 01/24716 | 4/2001 |
| WO | WO 03/077055 | 9/2003 |
| WO | WO 2004/110558 | 12/2004 |

OTHER PUBLICATIONS

Invitation to Pay Additional Fees; PCT/US2006/034449; mailed Feb. 19, 2007.

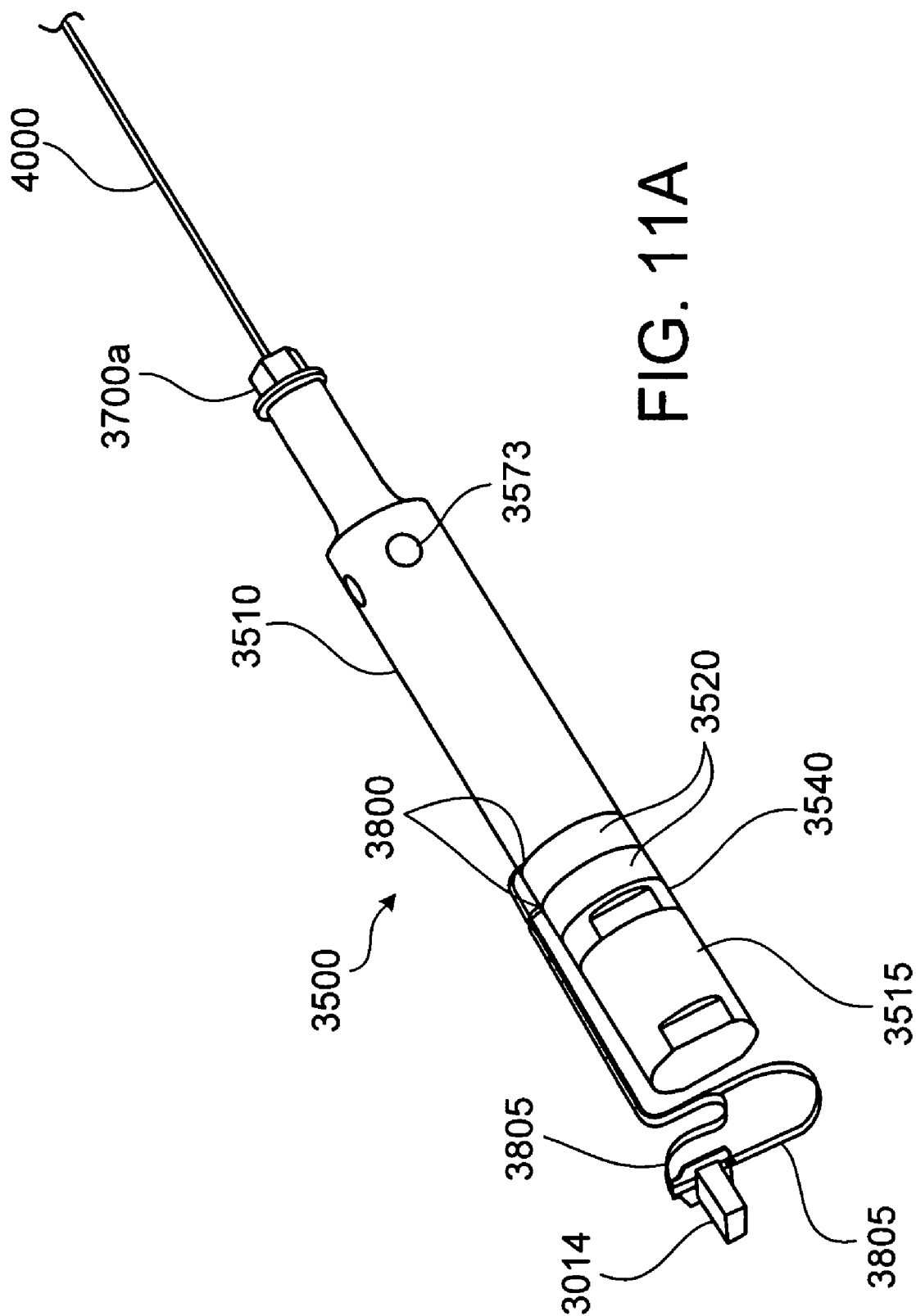

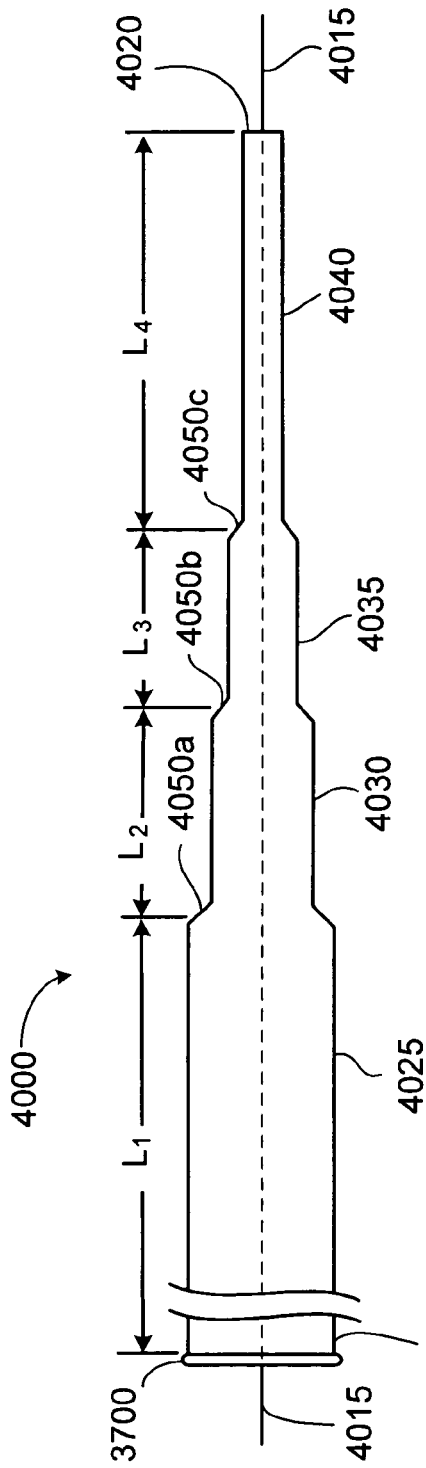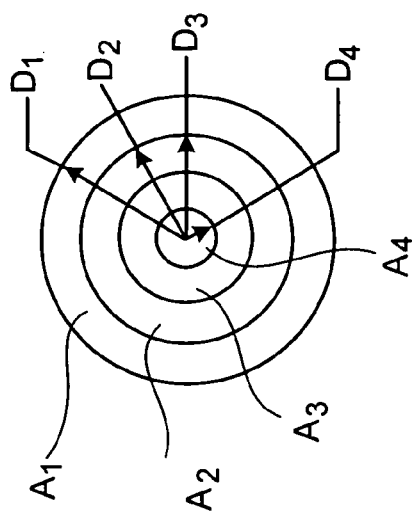
FIG. 13A
FIG. 13B

ULTRASOUND MEDICAL DEVICES, SYSTEMS AND METHODS

CROSS-REFERENCE TO RELATED APPLICATIONS

This application claims the benefit of U.S. application Ser. No. 60/714,456, filed on Sep. 6, 2005, which is incorporated by reference herein.

TECHNICAL FIELD

This description relates to ultrasound medical devices, systems and methods.

BACKGROUND

An ultrasound medical device can be used to treat a subject (e.g., a human) having certain conditions. Typically, a portion of the ultrasound medical device is disposed within the subject, and the ultrasound medical device is activated so that the portion of the ultrasound medical device disposed within the subject vibrates at an ultrasonic frequency. The ultrasonic vibrations can treat the condition (e.g., by breaking up tissue in the subject).

For example, an ultrasound medical device can be used to treat an occluded blood vessel in a subject by disposing a portion of the ultrasound medical device within the blood vessel at a location adjacent the occlusion. The ultrasound medical device is subsequently activated so that the portion of the device adjacent the occlusion vibrates at an ultrasonic frequency, and the ultrasonic vibrations can break up the occlusion.

SUMMARY

In general, the invention relates to ultrasound medical devices, systems and methods.

In one aspect of the invention, a method includes determining an absolute value of a first input to a voltage controlled oscillator (VCO) that is in electrical communication with an acoustic assembly of an ultrasound medical device. If the absolute value of the first input to the VCO is in a first range, a second input to the VCO is maintained. If the absolute value of the first input to the VCO is in a second range, the second input to the VCO is adjusted by a first voltage. If the absolute value of the first input to the VCO is in a third range, the second input to the VCO is adjusted by a second voltage, the second voltage being greater than the first voltage.

In an additional aspect of the invention, a computer program product, tangibly embodied in an information carrier, for executing instructions, is operable to cause a machine to determine an absolute value of an error input to a voltage controlled oscillator (VCO) that is in electrical communication with an acoustic assembly of an ultrasound medical device. If the absolute value of the first input to the VCO is in a first range, a second input to the VCO is maintained. If the absolute value of the first input to the VCO is in a second range, the second input to the VCO is adjusted by a first voltage. If the absolute value of the first input to the VCO is in a third range, the second input to the VCO is adjusted by a second voltage, the second voltage being greater than the first voltage.

In another aspect of the invention, an ultrasound medical system includes an ultrasound medical device includes an ultrasound vibration device including an acoustic assembly, a voltage controlled oscillator (VCO) in electrical communication with the ultrasound vibration device, and a control unit configured to determine an absolute value of an error input to the VCO that is in electrical communication with the ultrasound vibration device. If the absolute value of the first input to the VCO is in a first range, a second input to the VCO is maintained. If the absolute value of the first input to the VCO is in a second range, the second input to the VCO is adjusted by a first voltage. If the absolute value of the first input to the VCO is in a third range, the second input to the VCO is adjusted by a second voltage, the second voltage being greater than the first voltage.

Embodiments can include one or more of the following features.

In some embodiments, the second voltage is at least about 5% greater than the first voltage.

In certain embodiments, the first voltage is configured to generate a change in an output frequency of a voltage generated by the VCO having an absolute value of at least about 20 Hz.

In some embodiments, the second voltage is configured to generate a change in an output frequency of the VCO of at least about 40 Hz.

In certain embodiments, the acoustic assembly has a resonant frequency, and the method further includes adjusting the first input to the VCO based on a change in the resonant frequency of the acoustic assembly.

In some embodiments, the resonant frequency is a harmonic of a fundamental resonant frequency of the acoustic assembly.

In certain embodiments, the acoustic assembly has a resonant frequency, and the method further includes determining the resonant frequency of the acoustic assembly.

In some embodiments, the ultrasound vibration device is an ultrasonic probe.

In certain embodiments, the computer program product further includes instructions to cause a machine to adjust the first input based on a change in a resonant frequency of the acoustic assembly.

In some embodiments, the computer program product further includes instructions to cause a machine to determine a resonant frequency of the acoustic assembly.

In certain embodiments, the control unit is further configured to adjust the first input based on a change in a resonant frequency of the acoustic assembly.

In some embodiments, the acoustic assembly is in electrical communication with the VCO.

In certain embodiments, the ultrasound vibration device further includes a wire coupled to the acoustic assembly.

Embodiments can include one or more of the following advantages.

Generally, the systems can be designed for relatively safe, easy and effective use.

The systems can be designed to allow for accurate and dynamic adjustments (e.g., in the output of the power supply) in the vibrational frequency of an acoustic assembly in the system so that the vibrational frequency of the acoustic assembly is appropriately matched to a resonant frequency (e.g., the fundamental resonant frequency or a harmonic of the fundamental resonant frequency) of the acoustic assembly. This can, for example, enhance the safety and/or enhance the efficiency of the systems. As an example, this design can reduce the possibility of the acoustic assembly vibrating at an inappropriate frequency for a given procedure. As another example, this design can reduce inefficiencies associated with a mismatch between the frequency at which the acoustic assembly is driven and the frequency at which the acoustic assembly should be driven to be appropriately matched to its resonant frequency.

The optional storage of one or more operational parameters in a memory located in the hand piece assembly can, for example, enhance the safety of systems that include the hand piece assembly. As an example, the operational parameters can identify the hand piece assembly and the procedures for which the hand piece assembly is properly used. As another example, the number of operational parameters input by a user can be reduced, thereby reducing the possibility of user error introduced by inputting.

Other aspects, features, and advantages will be apparent from the description and claims.

DESCRIPTION OF DRAWINGS

FIGS. 11A to 11C are schematic perspective, side, and sectional views, respectively, of a portion of hand piece assembly.

FIGS. 13A and 13B are schematic side and end views, respectively, of a wire.

Like reference symbols in the various drawings indicate like elements.

DETAILED DESCRIPTION

Figure 1:
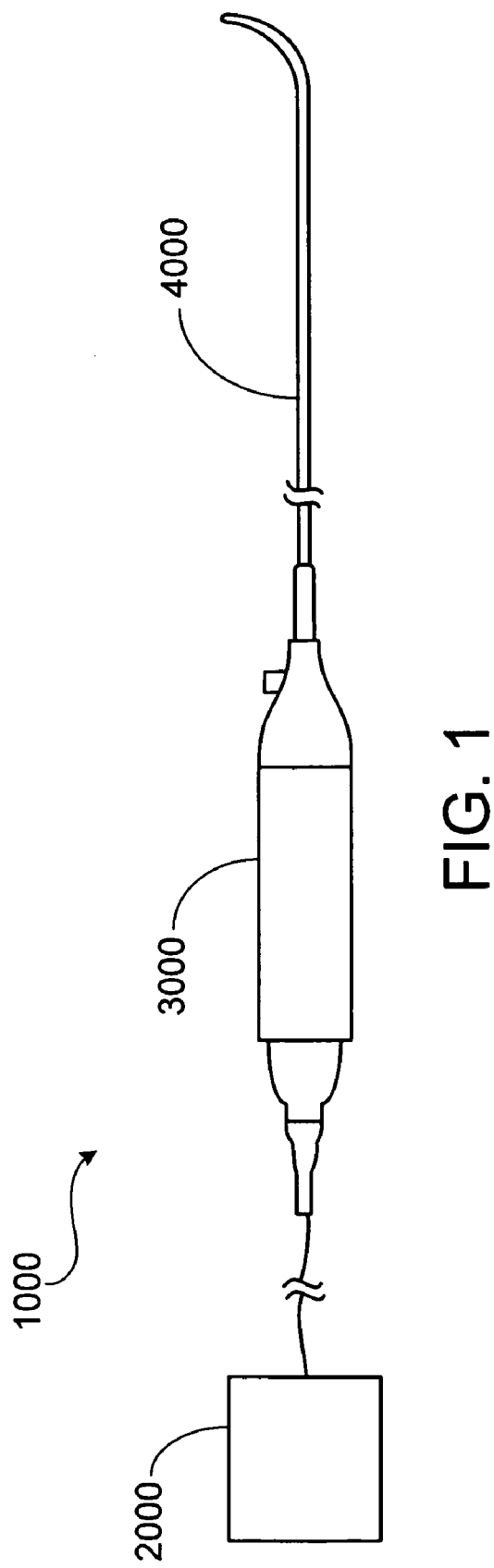
FIG. 1 is a schematic drawing of an ultrasound vibration system.

FIG. 1 shows an ultrasound vibration system 1000 that includes a power supply 2000, a hand piece assembly 3000 and an Ti-6A1-4V titanium wire 4000. Power supply 2000 is in electrical communication with hand piece assembly 3000, and hand piece assembly 3000 is mechanically coupled with wire 4000. As explained in detail below, power supply 2000 provides electrical energy (e.g., an oscillating voltage) to hand piece assembly 3000, and hand piece assembly 3000 converts this electrical energy to mechanical energy in the form of ultrasonic vibrations in an acoustic horn assembly 3500 (shown in FIG. 8) of hand piece assembly 3000 (e.g., ultrasonic vibrations at a resonant frequency of acoustic horn assembly 3500 of hand piece assembly 3000). The ultrasonic vibrations within acoustic horn assembly 3500 of hand piece assembly 3000 are transferred to wire 4000. Without wishing to be bound by theory, it is believed that the ultrasonic vibrations of wire 4000 can effect biological material (e.g., tissue, plaque, thrombus, kidney stones, biliary stones, etc.) in a subject directly, indirectly or both. It is believed that direct effects of wire 4000 on the biological material can involve wire 4000 directly contacting the biological material as wire 4000 vibrates, and/or wire 4000 creating ultrasonic vibrations in body fluid (e.g., blood) adjacent wire 4000 that are directly communicated to the biological material. It is believed that an indirect effect of wire 4000 on the biological material can involve the creation of bubbles in the body fluid (e.g., blood) adjacent the biological material, where the bubbles expand and collapse to create a hydraulic shock in the body fluid that is communicated to the biological material. This expansion and collapse of the bubbles in the body fluid is commonly referred to as cavitation.

Figure 2:
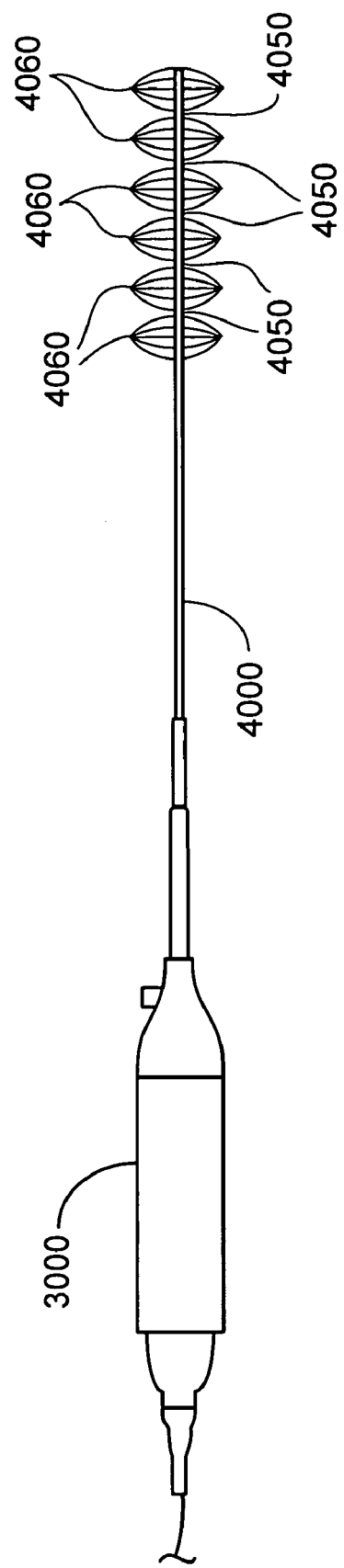
FIG. 2 is a schematic diagram of a portion of an ultrasound vibration system when activated.

FIG. 2 shows a representation of wire 4000 while vibrating. The vibrations in wire 4000 include nodes 4050 and anti-nodes 4060. Nodes 4050 are locations of minimum amplitude vibration of wire 4000, and anti-nodes 4060 are locations of maximum amplitude vibration of wire 4000.

The type of vibrational modes in wire 4000 are generally selected based on the intended use of ultrasound vibration system 1000 (e.g., the condition to be treated with system 1000). In general, the vibrations of wire 4000 can be transverse modes (modes for which the vibration is perpendicular to the longitudinal axis of wire 4000), longitudinal modes (modes for which the vibration is parallel to the longitudinal axis of wire 4000), or combinations thereof. FIG. 2 shows an embodiment where wire 4000 is undergoing transverse vibration. In some embodiments, however, one or more portions of wire 4000 can undergo transverse vibration while one or more other portions of wire 4000 undergo longitudinal vibration. For example, when breaking up an occlusion in a blood vessel, it may be desirable for the distal end of wire 4000 to undergo longitudinal vibration (to allow wire 4000 to penetrate into the occlusion) and for a more proximal portion of wire 4000 (e.g., the portion of wire 4000 proximally adjacent the distal end of wire 4000) to undergo transverse vibration (to break up the occlusion).

In general, the spacing of nodes 4050 and anti-nodes 4060 is selected based on the intended use of ultrasound vibration system 1000 (e.g., the condition to be treated with system 1000). Generally, nodes 4050 can be evenly spaced or unevenly spaced, and anti-nodes 4060 can be evenly spaced or unevenly spaced. In some embodiments, some of nodes 4050 are evenly spaced and some of nodes 4050 are unevenly spaced. In certain embodiments, some of anti-nodes 4060 are evenly spaced, and some of anti-nodes 4060 are unevenly spaced. FIG. 2 shows an embodiment where nodes 4050 are evenly spaced, and anti-nodes 4060 are evenly spaced.

Generally, the number of nodes 4050 and anti-nodes 4060 present along wire 4000 is selected based on the intended use of system 1000 (e.g., the condition to be treated with system 1000). As an example, FIG. 2 shows an embodiment where there are five nodes 4050 and six anti-nodes 4060 present along wire 4000. In some embodiments, there can be fewer than five (e.g., one, two, three, four) nodes 4050 or more than five (e.g., six, seven, eight, nine, 10) nodes 4050 present along wire 4000. In certain embodiments, there can be fewer than six (e.g., one, two, three, four, five) nodes 4060 or more than six (e.g., seven, eight, nine, 10) nodes 4060 present along wire 4000.

The amplitude of anti-nodes 4060 is generally selected based on the intended use of system 1000 (e.g., the condition to be treated with system 1000). In some embodiments, the amplitude of anti-nodes 4060 can be at least about five microns (e.g., at least about 10 microns, at least about 15 microns, at least about 20 microns, at least about 25 microns) and/or at most about 500 microns (e.g., at most about 400 microns, at most about 300 microns, at most about 250 microns). In certain embodiments, the amplitude of anti-nodes 4060 can be from about 10 microns to about 500 microns (e.g., from about 15 microns to about 400 microns, from about 20 microns to about 300 microns, from about 25 microns to about 250 microns).

In general, the frequency of the vibrations in wire 4000 is selected based on the intended use of system 1000 (e.g., the condition to be treated with system 1000). In some embodiments, the frequency of the vibrations in wire 4000 is at least about 10 kHz (e.g., at least about 15 kHz, at least about 20 kHz, at least about 30 kHz) and/or at most about 100 kHz (e.g., at most about 90 kHz, at most about 80 kHz, at most about 70 kHz). In certain embodiments, the frequency of the vibrations in wire 4000 is from about 10 kHz to about 100 kHz (e.g., from about 15 kHz to about 90 kHz, from about 20 kHz to about 80 kHz, from about 30 kHz to about 70 kHz, from about 35 kHz to about 45 kHz, from about 37 kHz to about 43 kHz, from about 39 kHz to about 41 kHz, about 40 kHz).

For a given design of hand piece assembly 3000 and configuration of wire 4000, the type and frequency of vibrations in wire 4000 (transverse and/or longitudinal), as well as the spacing, number and amplitude of anti-nodes 4060, is determined by the frequency of the output voltage of power supply 2000. In general, the frequency of the output voltage of power supply 2000 is at least about 10 kHz (e.g., at least about 15 kHz, at least about 20 kHz, at least about 30 kHz) and/or at most about 100 kHz (e.g., at most about 90 kHz, at most about 80 kHz, at most about 70 kHz). In some embodiments, the frequency of the output voltage of power supply 2000 is from about 10 kHz to about 100 kHz (e.g., from about 15 kHz to about 90 kHz, from about 20 kHz to about 80 kHz, from about 30 kHz to about 70 kHz, from about 35 kHz to about 45 kHz, from about 37 kHz to about 43 kHz, from about 39 kHz to about 41 kHz, about 40 kHz).

Figure 3:
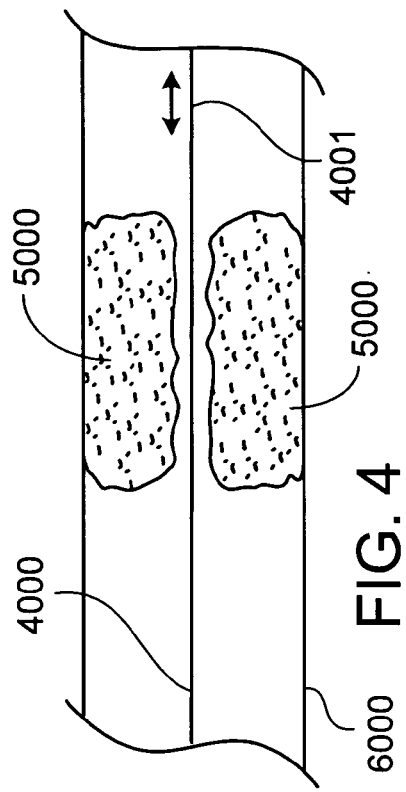
FIGS. 3 through 6 are schematic drawings of a method of using an ultrasound vibration system to treat an occluded blood vessel.
Figure 4:
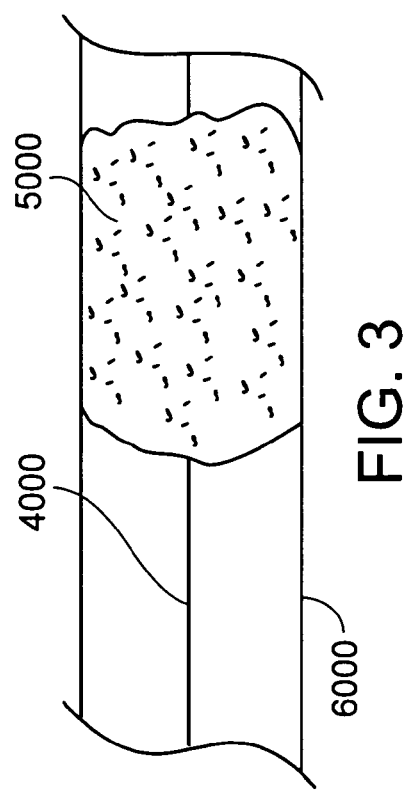
Figure 5:
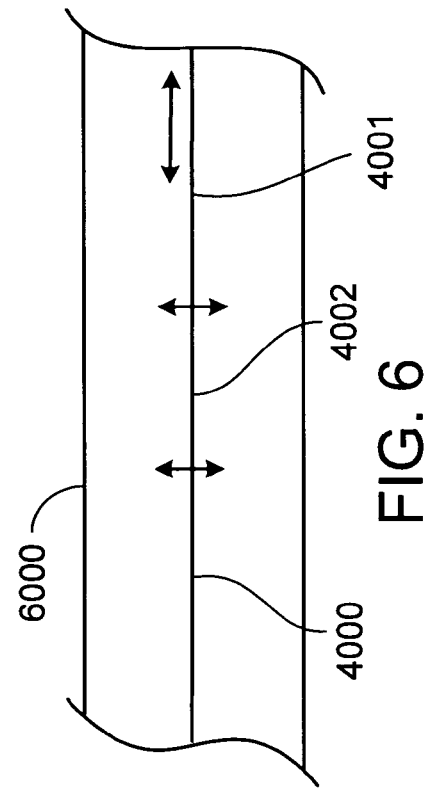
Figure 6:
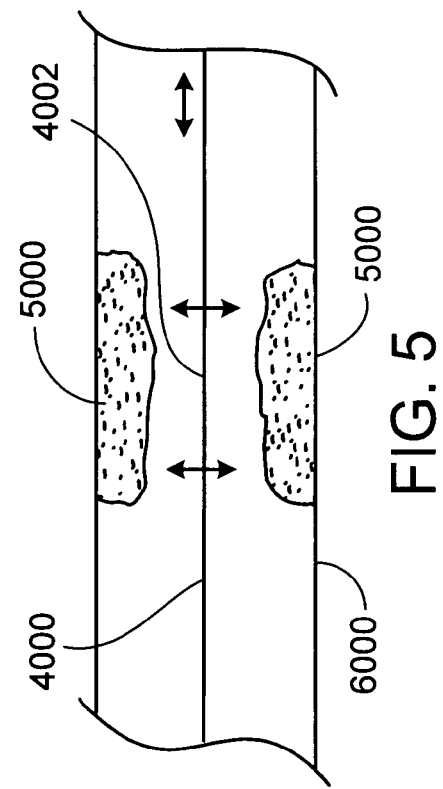

Ultrasound vibration system 1000 can be used to treat a variety of conditions. For example, FIGS. 3-6 show an embodiment in which system 1000 is used to treat an occlusion 5000 in a blood vessel 6000 of a subject (e.g., a human). Referring to FIG. 3, wire 4000 is disposed within blood vessel 6000 at a location that is adjacent occlusion 5000. FIG. 4 shows that, after power supply 2000 is activated to provide electrical energy to hand piece assembly 3000, a distal end 4001 of wire 4000 undergoes longitudinal vibration, allowing wire 4000 to penetrate into occlusion 5000. As shown in FIGS. 5 and 6, a portion 4002 of wire 4000 that is proximal to distal end 4001 undergoes transverse vibration to break up occlusion 5000.

Figure 7A:
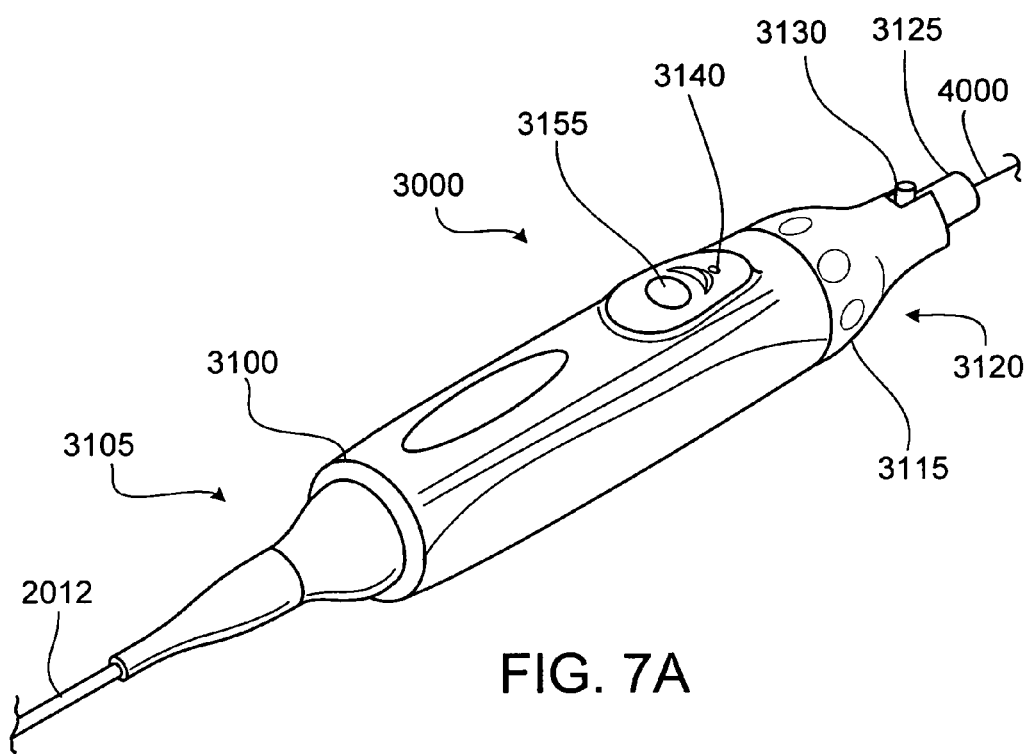
FIGS. 7A and 7B are schematic perspective and top views, respectively, of a hand piece assembly.
Figure 7B:
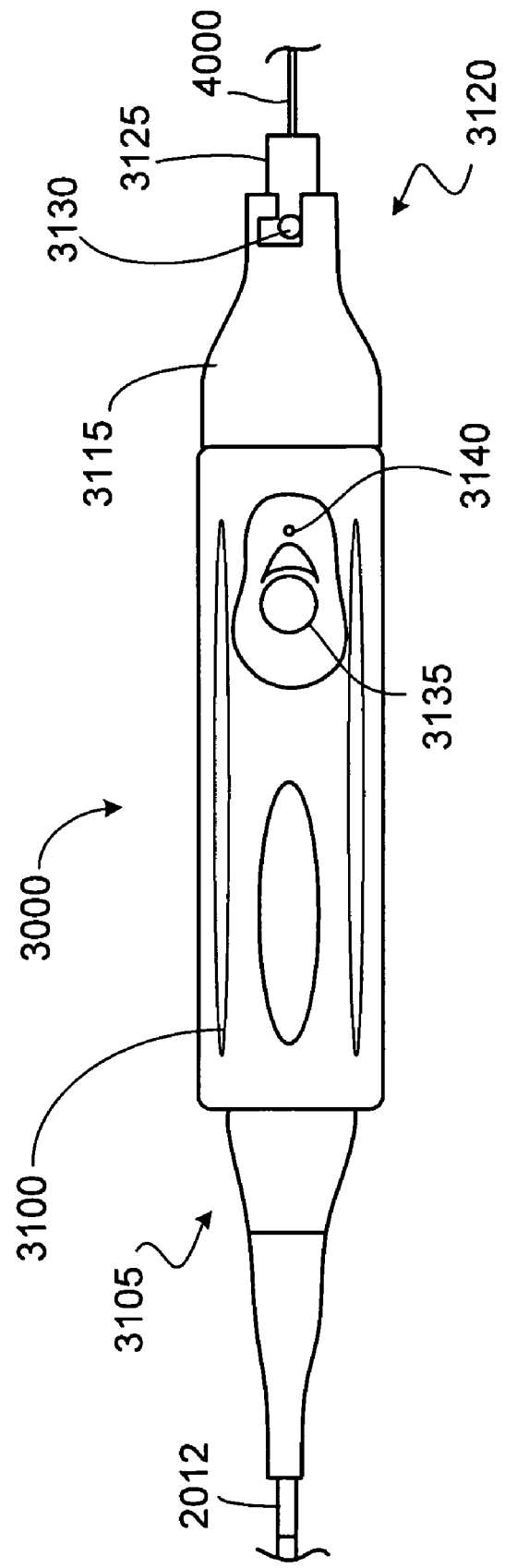

Referring to FIGS. 7A and 7B, hand piece assembly 3000 includes a hand piece body 3100 connected to power supply 2000 at a proximal end 3105 by a multi-wire cable 2012 and threadably connected to a nose cone 3115 at a distal end 3120. An irrigation coupler hub 3125 is attached to nose cone 3115 and includes an irrigation coupler port 3130 for connection to a fluid source (e.g., for use in embodiments where a catheter surrounds wire 4000 so that a fluid can flow between wire 4000 and the catheter to irrigate the region adjacent the biological material being treated and/or to cool the wire during use). Wire 4000 extends longitudinally from distal end 3120 of hand piece assembly 3000 through a central bore along coupler hub 3125. Hand piece body 3100 includes a power switch 3135 to control power supply 2000 and an indicator light 7140 to indicate the operational status of system 1000. Power switch 3135 is a touch switch for which a first push places switch 3135 in a first state (e.g., power supply 2000 on) and a second push places switch 3135 in a second state (e.g., power supply 2000 off).

Figure 8:
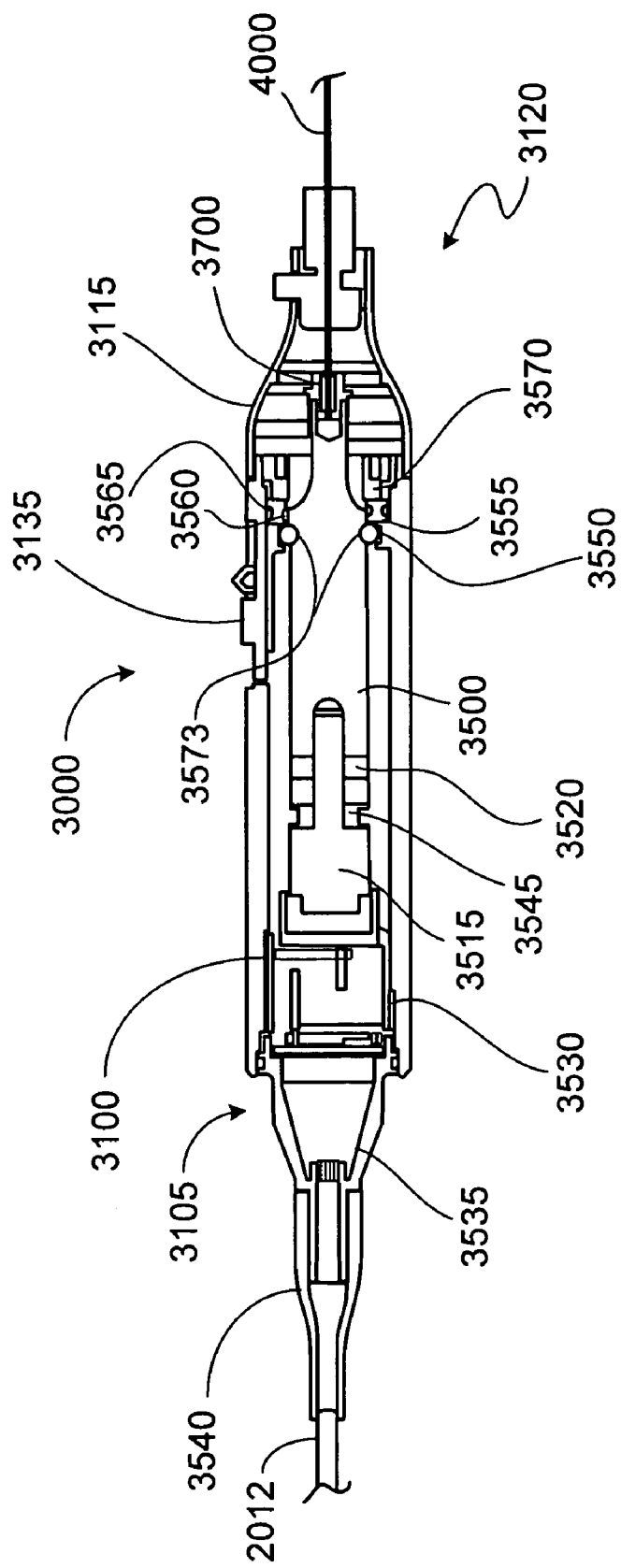
FIG. 8 is a sectional view of the hand piece assembly of FIGS. 7A and 7B.
Figure 9A:
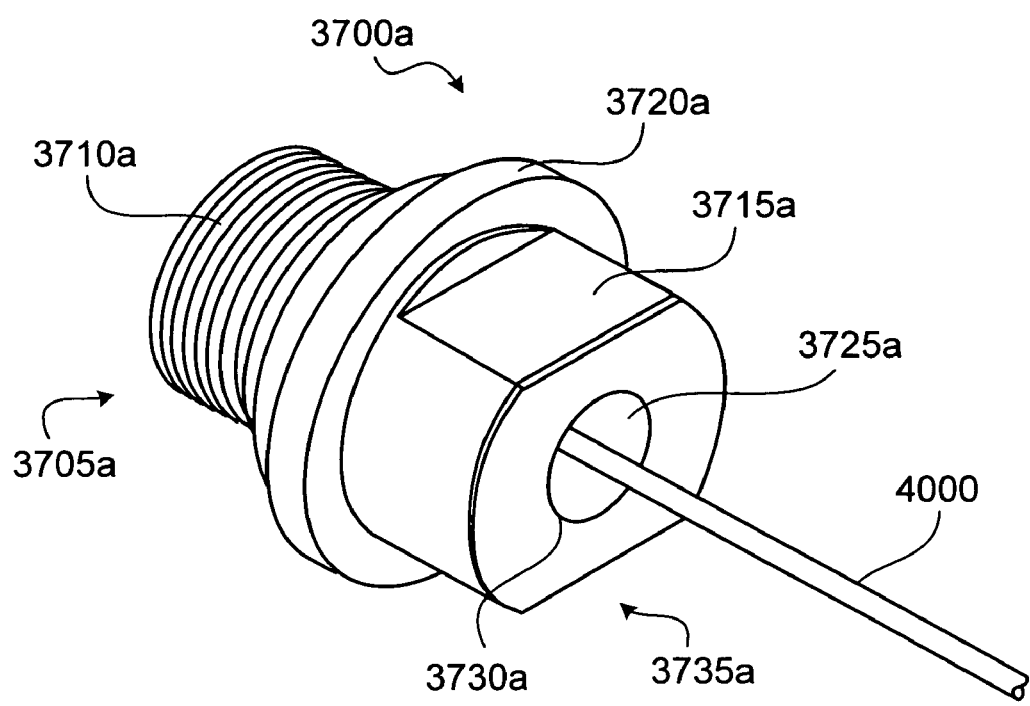
FIGS. 9A to 9D are perspective, alternative perspective, side and sectional views, respectively, of an acoustic coupler.
Figure 9B:
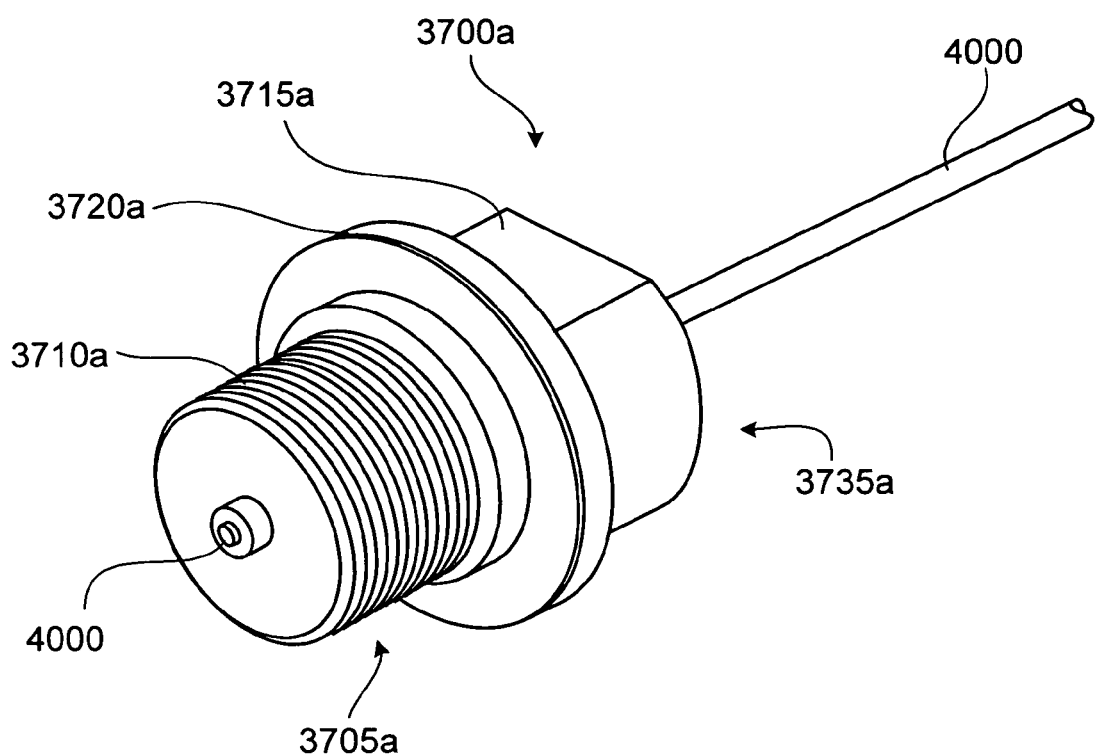
Figure 9C:
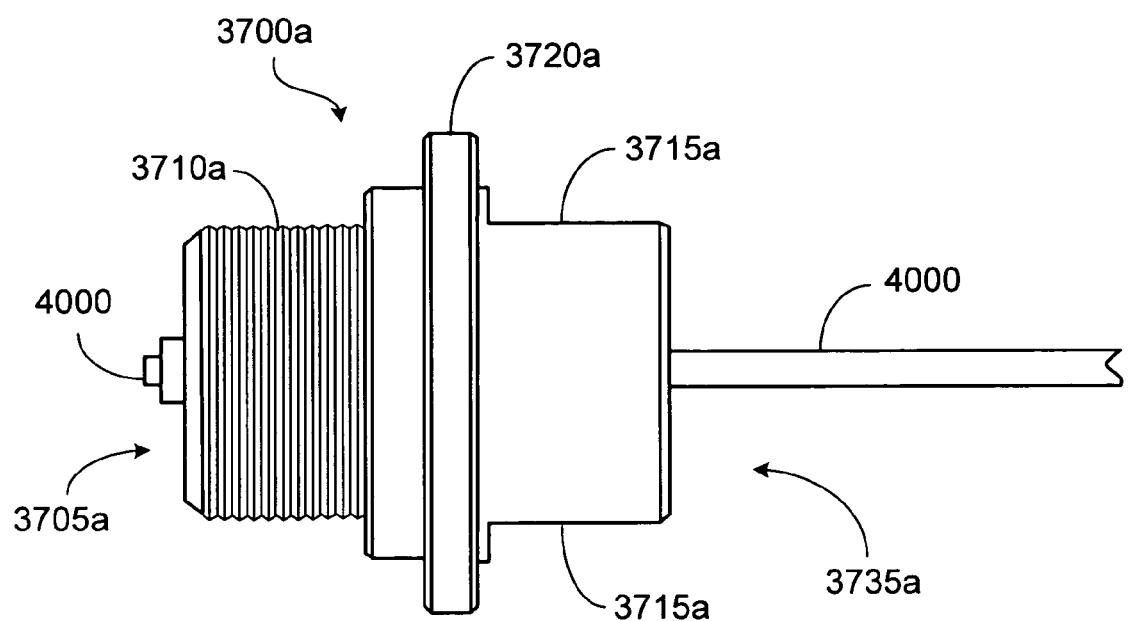
Figure 9D:
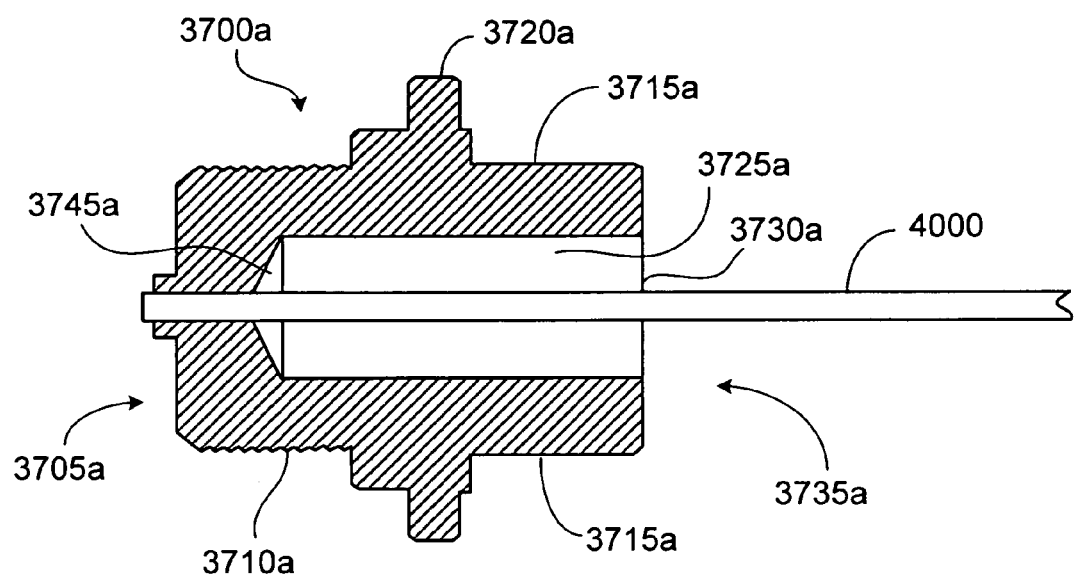

FIG. 8 shows the internal components of the hand piece assembly 3000 including an acoustic horn assembly 3500 generally extending longitudinally from proximal end 3105 of hand piece body 3100 toward distal end 3120 of hand piece body 3100. Acoustic horn assembly 3500 includes a distal horn 3510, a backmass 3515 and a plurality of piezoelectric transducers (e.g., piezoceramic rings) 3520 disposed between horn 3510 and backmass 3515. Distal horn 3510 is mechanically connected (e.g., via a threaded connection) to a proximal side of an acoustic coupler 3700, and wire 4000 is metallurgically bonded to a distal side of acoustic coupler 3700. With this arrangement, during use of system 1000, power supply 2000 provides electrical energy in the form of an oscillating voltage to piezoelectric transducers 3520, and piezoelectric transducers 3520 convert the electrical energy to mechanical energy in the form of vibrational energy that is transmitted to wire 4000 via acoustic coupler 3700.

Acoustic horn assembly 3500 is secured to proximal end 3105 of hand piece body 3100 by a proximal mount 3530 configured to house the backmass 3515. A tapered fitting 3535 is attached to the proximal end 3105 and extends from the proximal mount 3530 to a flexible collar 3540 surrounding the terminal end of cable 2012. A spacer 3545 is disposed between piezoelectric transducers 3520 and the backmass 3515. Acoustic horn assembly 3500 is secured to distal end 3120 of hand piece body 3100 by a plurality of ball bearings 3550, a mounting ring 3555 including silicone o-rings 3560, 3565 along inner and outer surfaces, respectively, and a front retainer ring 3570. Ball bearings 3550, mounting ring 3555, and front retainer ring 3570 are all disposed between hand piece body 3100 and distal horn 3510. Dimples 3573 are positioned along distal horn 3510 and receive ball bearings 3550. Front retainer ring 3570 includes external threads engaging corresponding internal threads of hand piece body 3100 such that rotation of retainer ring 3570 compresses acoustic horn assembly 3500 and piezoelectric transducers 3520. Retainer ring 3570 can include spanner wrench holes 3575 for receiving a tool to permit rotation of ring 3570 to a predetermined torque.

As noted above, acoustic coupler 3700 is metallurgically bonded (e.g., welded) to wire 4000 to allow vibrational energy to be transmitted from piezoelectric transducers 3520 to wire 4000. Generally, acoustic coupler 3700 and wire 4000 can be metallurgically bonded at any desired location within acoustic coupler 3700.

As an example, FIGS. 9A through 9D show an embodiment in which an acoustic coupler 3700*a* is metallurgically bonded to wire 4000 at a location 3745*a* adjacent a proximal end 3705*a* of acoustic coupler 3700*a*. Acoustic coupler 3700*a* includes external threads 3710*a* along a proximal end 3705*a* to threadably connect to corresponding internal threads of the distal horn 3510 (FIG. 8). Alternatively or additionally, acoustic coupler 3700*a* can include internal threads 3710*a* along a proximal end 3705*a* to threadably connect to corresponding external threads of the distal horn 3510. Wrench flats 3715*a* permit rotation of acoustic coupler 3700*a* against the distal horn 3510 to a predetermined torque. A flange 3720*a* extends around a central portion of coupler 3700*a* and engages distal horn 3510 when attached thereto. A main bore 3725*a* extends from an opening 3730*a* at a distal end 3735*a* of coupler 3700*a* to a proximal bore 3740*a*. Wire 4000 extends through bores 3725*a* and 3740*a*, and, as noted above, is bonded with coupler 3700*a* at location 3745*a*.

Figure 10A:
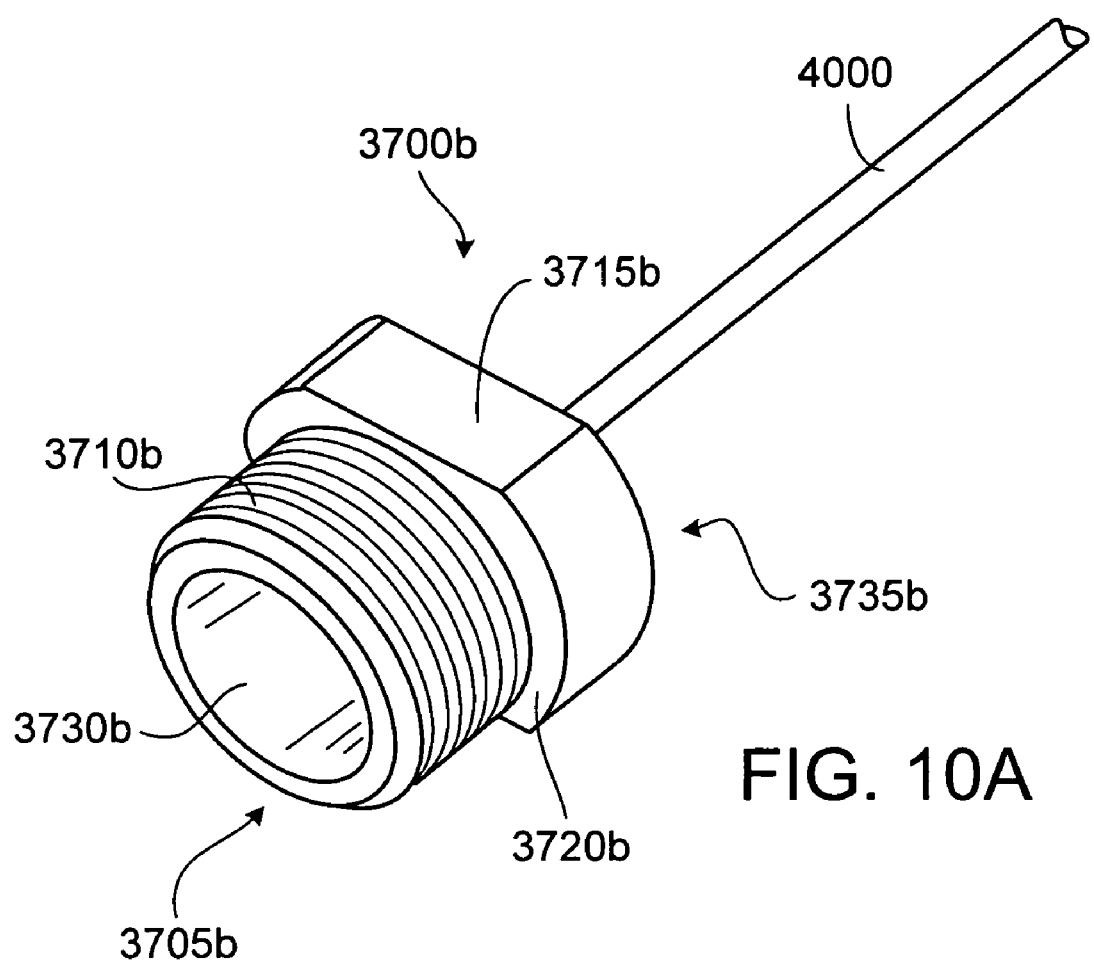
FIGS. 10A to 10C are perspective, alternative perspective, and cross sectional views, respectively, of another acoustic coupler.
Figure 10B:
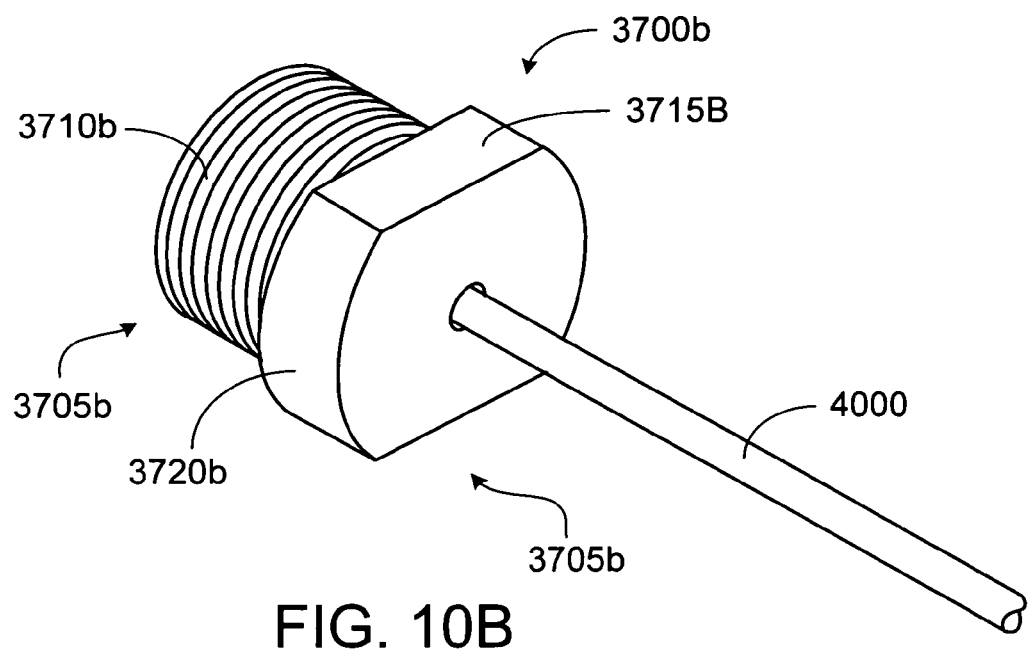
Figure 10C:
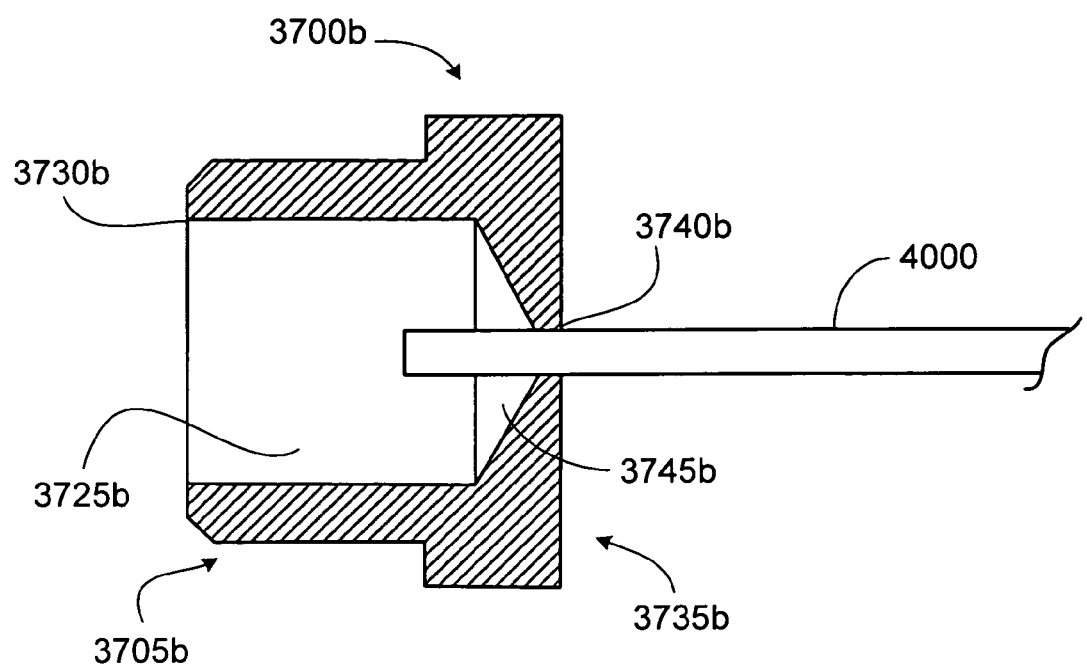

As another example, FIGS. 10A through 10C show an embodiment in which an acoustic coupler 3700*b* is metallurgically bonded to wire 4000 at a location 3745*b* adjacent a distal end 3735*b* of acoustic coupler 3700*b*. Acoustic coupler 3700*b* includes external threads 3710*b* to threadably connect to corresponding internal threads of distal horn 3510 (FIG. 8). Wrench flats 3715*b* permit rotation of coupler 3700*b* against distal horn 3510 to a predetermined torque. A flange 3720*b* extends around a central portion of coupler 3700*b* and engages distal horn 3510 when attached thereto. A main bore 3725*b* extends from an opening 3730*b* at a proximal end 3705*b* of coupler 3700*b* to a distal bore 3740*b*. Wire 4000 extends through bores 3725*b* and 3740*b* and, as noted above, is bonded with coupler 3700*b* at location 3745*b*.

Typically, wire 4000 is metallurgically bonded with the acoustic coupler as follows. Wire 4000 is disposed within the acoustic coupler. The acoustic coupler and wire 4000 are then heated at a region where the metallurgical bond is desired (e.g., adjacent a proximal end of the acoustic coupler, adjacent a distal end of the acoustic coupler). Heating can be achieved using a variety of techniques, such as, for example, welding (e.g., arc welding). Generally, the heated region of wire 4000 and the acoustic coupler are brought to a temperature sufficient to form a metallurgical bond without substantially altering the physical properties of wire 4000 and the acoustic coupler.

In some embodiments, locations of bonding 3745*a*, 3745*b* are relatively close to an anti-node 4060 of the ultrasonic vibrations of wire 4000 during use of system 1000. Without wishing to be bound by theory, it is believed that such an arrangement of a bond location can improve the ultrasonic transfer efficiency of system 1000 and/or decrease localized heating in system 1000 (e.g., localized heating in the ultrasonic coupler and/or wire 40000 during use of system 1000).

In certain embodiments, the diameter of openings 3730*a*, 3730*b* in couplers 3700*a*, 3700*b* is about the same as the cross-sectional diameter of wire 4000. For example, in some embodiments, the cross-sectional diameter of wire 4000 is at least about 75% (e.g., at least about 85%, at least about 95%) of the cross-sectional diameter of openings 3730*a*, 3730*b*. Without wishing to be bound by theory, it is believed that using a cross-sectional diameter for openings 3730*a*, 3730*b* that is similar to the cross-sectional diameter of wire 4000 can improve the ultrasonic transfer efficiency of system 1000.

As used herein, the term "ultrasonic transfer efficiency" is the ratio X:Y, where X is the amount of electrical energy (in the form of an oscillating voltage) output by power supply 2000 to hand piece assembly 3000, and Y is the amount of mechanical energy in wire 4000 (in the form of ultrasonic vibrations in wire 4000). In certain embodiments, system 1000 has an ultrasonic transfer efficiency of about 1:10 (or about ten percent) or greater. System 1000 can, for example, have an ultrasonic transfer efficiency of about 1:110 (or about ten percent) to about 1:2 (or about 50 percent).

In some embodiments, after assembly and prior to wire 4000 being bent, the combined length of wire 4000 and the acoustic coupler in the longitudinal direction of wire 4000 (referred to as the relevant length) is equal to about five wavelengths, about 11 wavelengths, or about 13 wavelengths of an ultrasonic vibration. For example, for coupler 3700*a*, the relevant length is the length of wire 4000 in the longitudinal direction, and, for coupler 3700*b*, the relevant length is the length from proximal end 3705*b* to the distal end of wire 4000. In certain embodiments, wire 4000 has a length substantially equal to the product of one-quarter wavelength and an odd multiplier (e.g., about 5¼ wavelengths, about 11¼ wavelengths, or about 13¼ wavelengths).

Figure 11B:
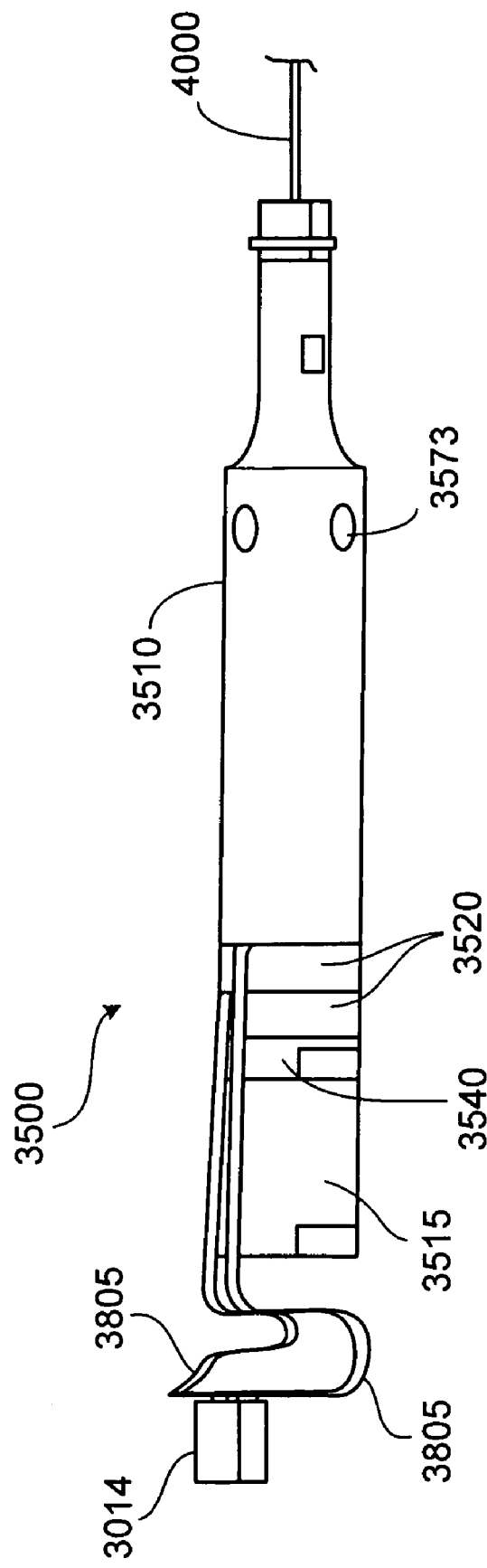
Figure 11C:
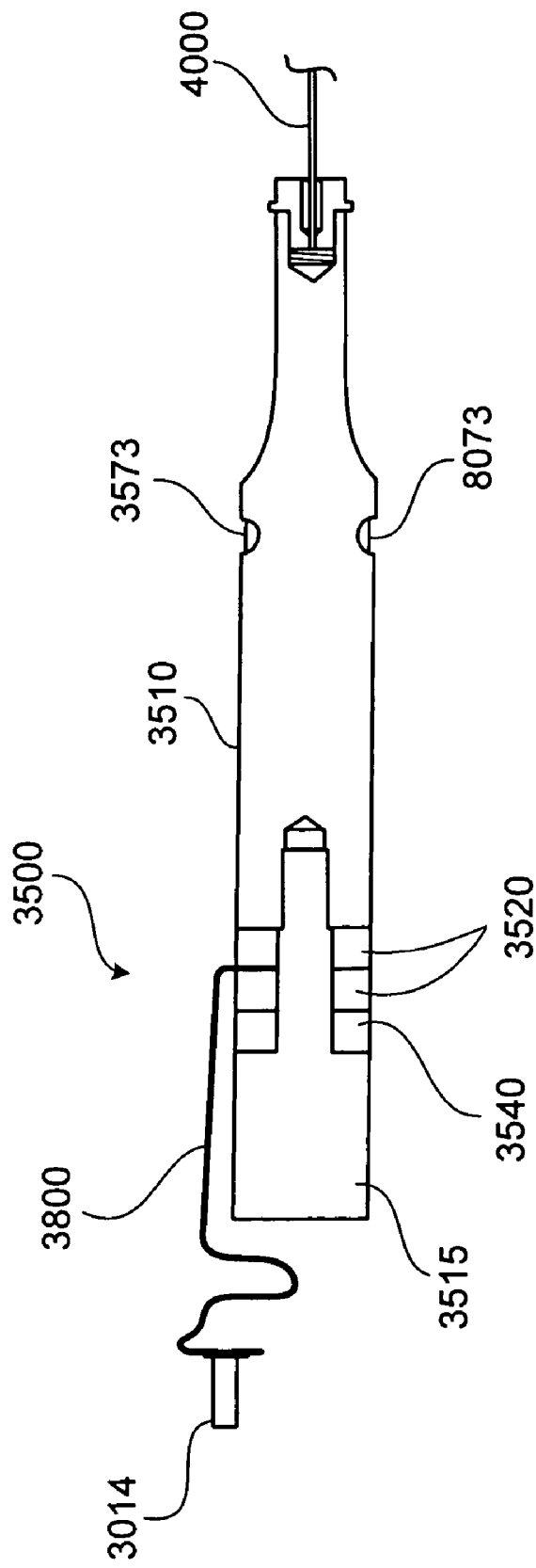
Figure 12A:
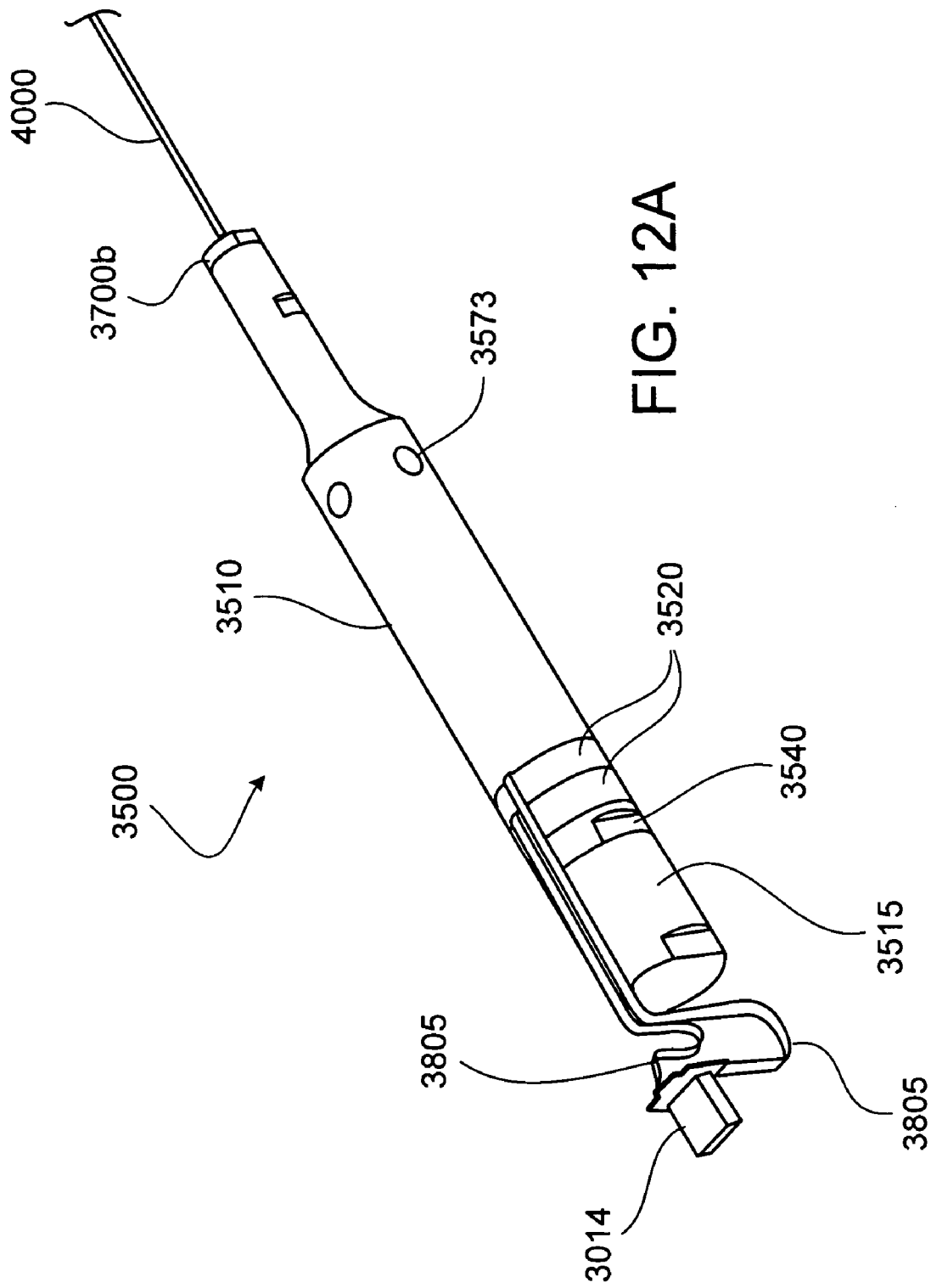
FIGS. 12A to 12C are schematic perspective, side, and sectional views, respectively, of a portion of another hand piece assembly.
Figure 12B:
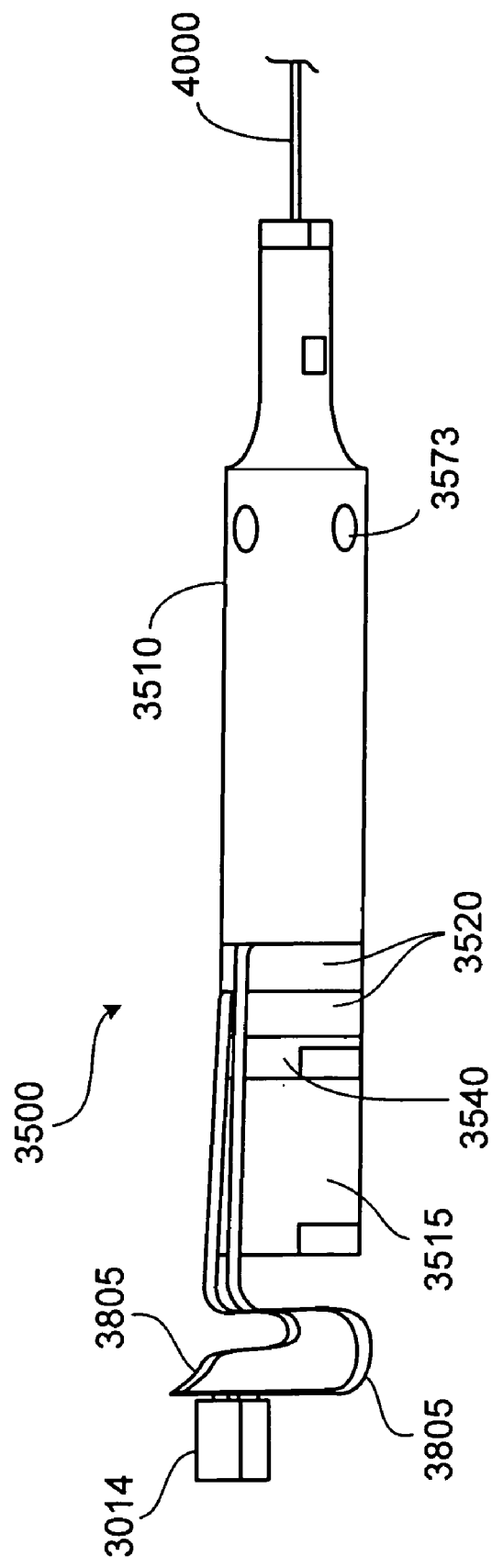
Figure 12C:
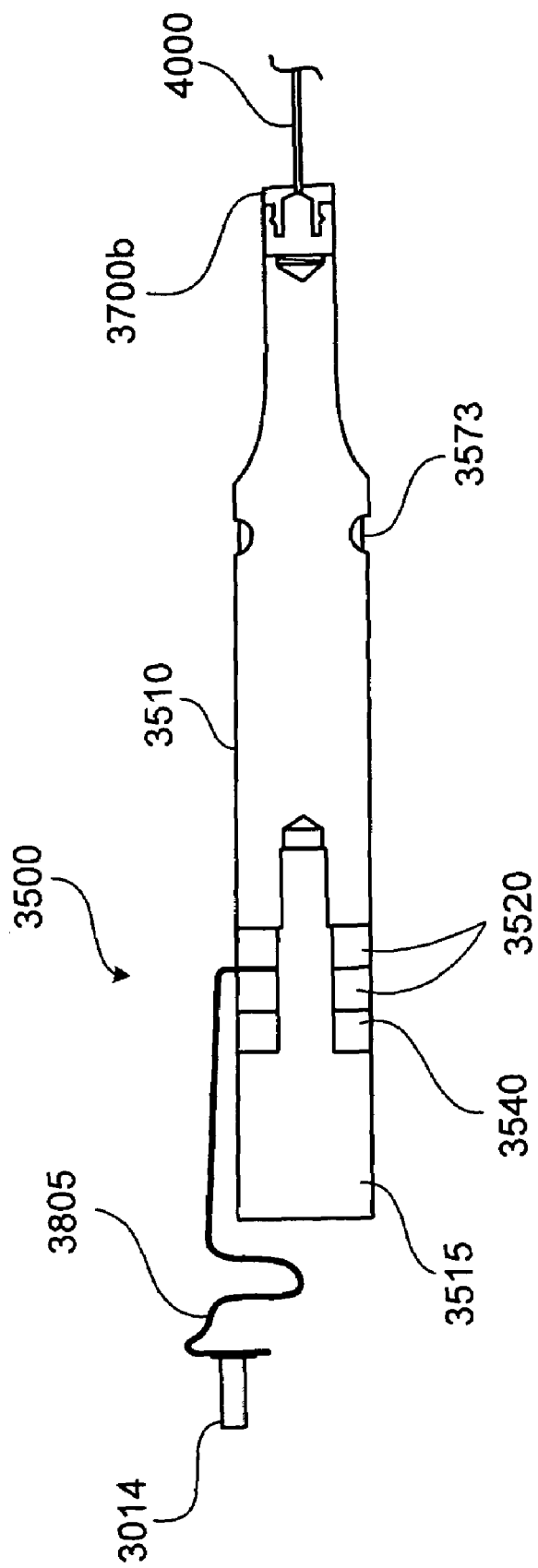

Typically, part of the path of electrical communication between piezoelectric transducers 3520 and power supply 2000 includes one or more electrodes and one or more leads. As an example, FIGS. 11A through 11C show acoustic horn assembly 3500 attached to coupler 3700*a*, electrodes 3800 in electrical communication with piezoelectric transducers 3520, and leads 3805 in electrical communication with electrodes 3800. As another example, FIGS. 12A though 12C show acoustic horn assembly 3500 attached to coupler 3700*b*, electrodes 3800 in electrical communication with piezoelectric transducers 3520, and leads 3805 in electrical communication with electrodes 3800. As also shown in FIGS. 11A through 12C, in some embodiments, leads 3805 connect to a memory 3014 in hand piece assembly 3000. Memory 3014 can transmit information to and from power supply 2000 over cable 2012 (see discussion below).

Examples of materials from which distal horn 3510 can be formed include metals (e.g., titanium, stainless steel, aluminum) and alloys.

Examples of materials from which backmass 3515 can be formed include metals (e.g., titanium, stainless steel) and alloys.

Generally, piezoelectric transducers can be formed of any appropriate materials. Examples of materials include piezoceramic materials, such as barium titanate and lead-zirconate-titanate. Suitable lead-zirconate-titanates are available commercially in a variety of compositions, including PZT-4 (Navy Type I), PZT-8 (Navy Type III).

In some embodiments, acoustic coupler 3700 is made from a metal (e.g., titanium, stainless steel, aluminum) and/or one or more alloys.

In general, electrodes 3800 can be formed of any sufficiently electrically conductive material. Exemplary materials include metals (e.g., nickel) and alloys (e.g., beryllium copper alloy, phosphor bronze alloy).

Referring to FIGS. 13A and 13B, (unbent) wire 4000 has a proximal end 4010, a distal end 4020 and a longitudinal axis 4015 that extends between ends 4010 and 4020. An acoustic coupler 3700 is adjacent proximal end 4010 of wire 4000.

Wire 4000 includes a series of transformer sections 4025, 4030, 4035, and 4040, across a plurality of transitions 4050a, 4050b, 4050c. Transformer sections 4025, 4030, 4035 and 4040 have diameters $D_1, D_2, D_3$ and $D_4$, lengths $L_1, L_2, L_3$ and $L_4$, and cross-sectional areas $A_1, A_2, A_3$ and $A_4$, all respectively. The physical properties and dimensions of transformer sections 4025, 4030, 4035 and 4040 impact the characteristics of the ultrasonic vibrations present in transformer sections 4025, 4030, 4035 and 4040. As a result, the properties of the ultrasonic vibrations (e.g., type of vibrations, frequency of vibrations, amplitude of vibrations, spacing between nodes, spacing between anti-nodes, number of nodes, number of anti-nodes) in each section of wire 4000 may be the same as or different from the properties of the ultrasonic vibrations in one or more other sections of wire 4000.

As an example, the ratio of the diameters of adjacent transformer sections of wire 4000 impacts the ratio of the amplitudes of the vibrations in these sections of wire 4000. For example, the ratio $D_1:D_2$ impacts the ratio of the amplitude of the vibrations in section 4025 to the amplitude of the vibrations in section 4030. In general, as the ratio of adjacent diameters increases (e.g., as the ratio $D_1:D_2$ increases), the ratio of the vibrational amplitude in the adjacent sections (e.g., the ratio of the vibrational amplitude in section 4025 to the vibrational amplitude in section 4030) also increases, and as the ratio of adjacent diameters decreases (e.g., as the ratio $D_1:D_2$ decreases), the ratio of the vibrational amplitude in the adjacent sections (e.g., the ratio of the vibrational amplitude of section 4025 to the vibrational amplitude in section 4030) also decreases.

As another example, the ratio A:B, where A is the ratio of the diameter to the length in one section of wire 4000 and B is the ratio of the diameter to the length in an adjacent section of wire 4000, impacts the potential for a transition from a longitudinal vibrational mode to a transverse vibrational when going from one section to the adjacent section. In general, as the ratio A:B increases (e.g., as the ratio $A_{4025}:B_{4030}$ increases), the potential for changing from a longitudinal vibrational mode to a transverse vibrational mode when going from the first section to the adjacent section (e.g., when going from section 4025 to section 4030) also increases, and as the ratio A:B decreases (e.g., as the ratio $A_{4025}:B_{4030}$ decreases), the potential for changing from a longitudinal vibrational mode to a transverse vibrational mode when going from the first section to the adjacent section (e.g., when going from section 4025 to section 4030) also decreases.

As a further example, the ratio of the flexural stiffness of adjacent transformer sections of wire 4000 also impacts the potential for going from a transverse vibrational mode to a longitudinal vibrational mode when going from one section of wire 4000 to the adjacent section of wire 4000. For example, going from a section of wire 4000 that has a relatively high flexural stiffness to an adjacent section of wire 4000 that has a relatively low flexural stiffness tends to increase the potential for changing from a longitudinal vibrational mode to a transverse vibrational mode, and going from a section of wire 4000 that has a relatively low flexural stiffness to an adjacent section of wire 4000 that has a relatively high flexural stiffness tends to decrease the potential for changing from a longitudinal vibrational mode to a transverse vibrational mode.

In general, consideration is also given to the intended use of system 1000 (e.g., the condition to be treated with system 1000) when selecting the dimensions of sections 4025, 4030, 4035 and 4040. As an example, the diameters of the transformer sections of wire should not be so large as to prevent wire 4000 from being able to fit within a desired portion (e.g., blood vessel) of a subject to be treated. As another example, the dimensions of wire 4000 can be selected so that wire 4000 is sufficiently flexible so that wire 4000 can be navigated through the relevant portions (e.g., the vasculature) of a subject to be treated. As a further example, wire 4000 should be sufficiently long so that the length of the portion of wire 4000 that is to undergo ultrasonic vibration during use of system 1000 (e.g., the length of sections 4025, 4030, 4035 and/or 4040) can reach a desired portion (e.g., an occlusion in a blood vessel) of a subject to be treated.

Wire 4000, as illustrated in FIGS. 13A and 13B, decreases in diameter from its proximal end toward its distal end. As a result, the amplitude of transverse vibrations in wire 4000 generally increase from its proximal end to its distal end, and the amplitude of longitudinal vibrations in wire 4000 generally decrease from its proximal end to its distal end. In some embodiments, wire 4000 is configured so that distal most section 4040 has the greatest transverse vibrational amplitude along wire 4000 and is sized such that section 4040 can reach the desired portion of the subject to be treated.

In general, wire 4000 can be prepared as desired. In some embodiments, wire 4000 is prepared using a process that involves little or no plastic deformation and/or work hardening of the material that forms wire 4000. In certain embodiments, wire 4000 is prepared using a process that creates little or no change in the mechanical and/or acoustic properties of the material that forms wire 4000.

An exemplary process for preparing wire 4000 is as follows. The transformer sections of wire 4000 are formed by grinding with a grinding wheel while exposing wire 4000 to a lubricant. The grinding wheel is made of a material that is sufficiently hard to reduce the diameter of wire 4000 to form the transformer sections of wire 4000. An example of a grinding wheel material is silicone carbide. Examples of lubricants that can be used include oils (e.g., water soluble oils).

Figure 14:
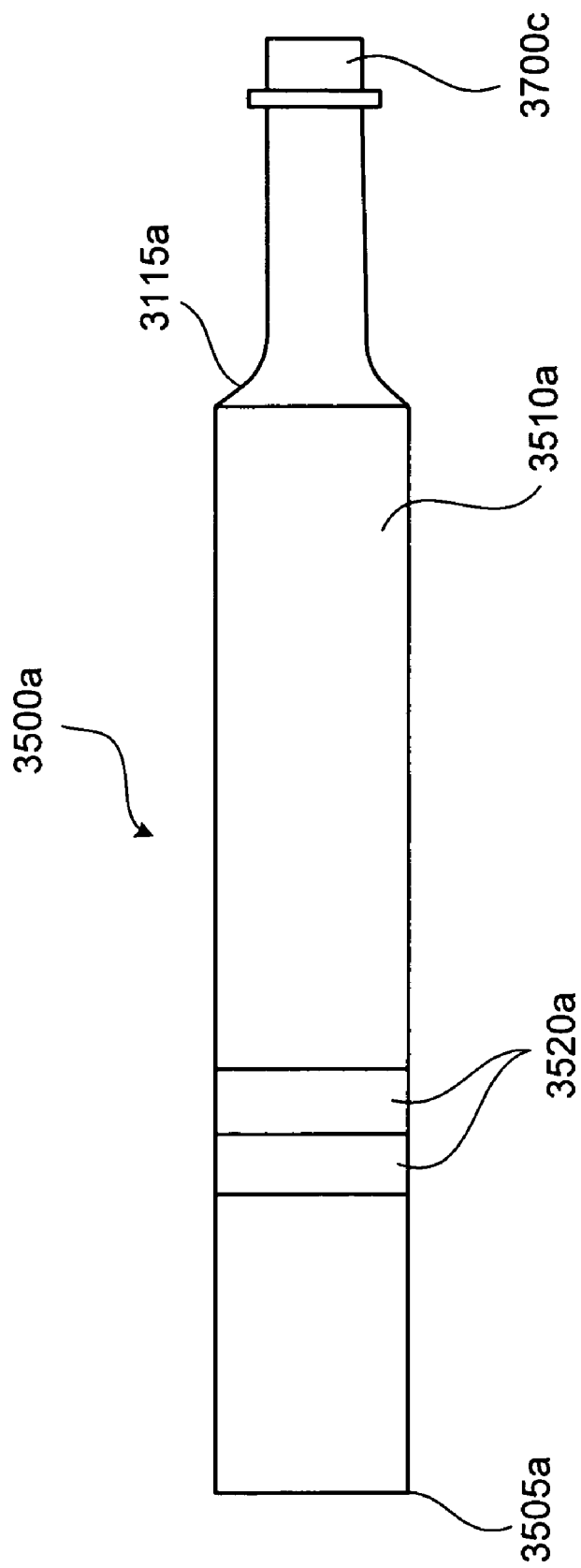
FIG. 14 is a schematic view of an acoustic horn as modeled with a finite element analysis.

In some embodiments, designing system 1000 can involve using finite element analysis to model one or more components in system 1000. For example, FIG. 14 shows an acoustic horn assembly 3500a as modeled using finite element analysis. Acoustic horn assembly 3500a has a proximal end 3505a, a distal horn 3510a, a nose cone 3115a and transducers 3520a. An acoustic coupler 3700c is attached to acoustic horn assembly 3500a. The average distance of transducers 3520a from proximal end 3505a is 1.12 inches. Distal horn 3510a engages hand piece body at the dimples along ball bearings (see discussion above) at a location that is 3.28 inches from proximal end 3505a. The distance from proximal end 3505a of acoustic horn assembly 3500a to a distal end 3735c of acoustic coupler 3700c is 4.68 inches. Proximal end 3505a is 3.507 inches from the proximal end of nose cone 3115a is 3.507.

Figure 15A:
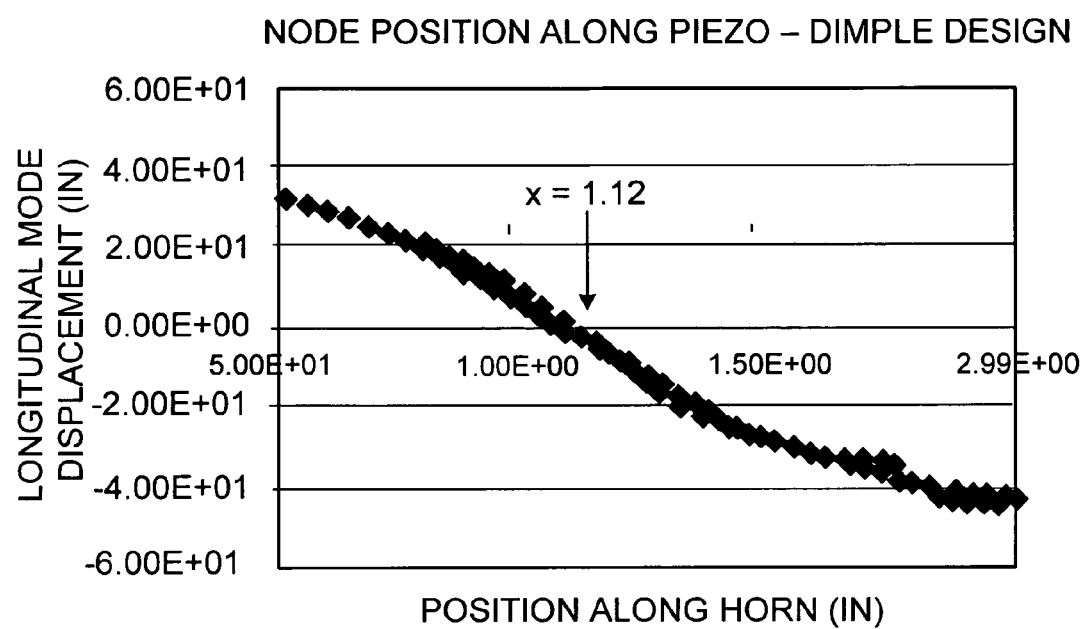
FIGS. 15A to 15C are graphs showing nodal displacement versus longitudinal position for a proximal portion, a distal portion, and the entire length of the acoustic horn, respectively, for the horn of FIG. 14 and achieved using finite element analysis.
Figure 15B:
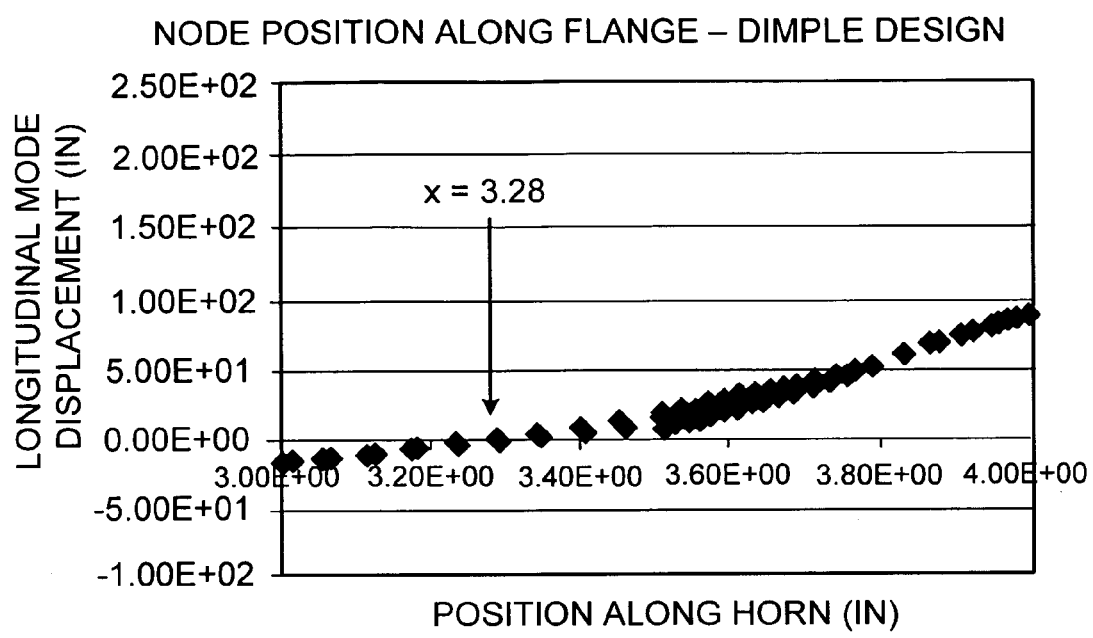
Figure 15C:
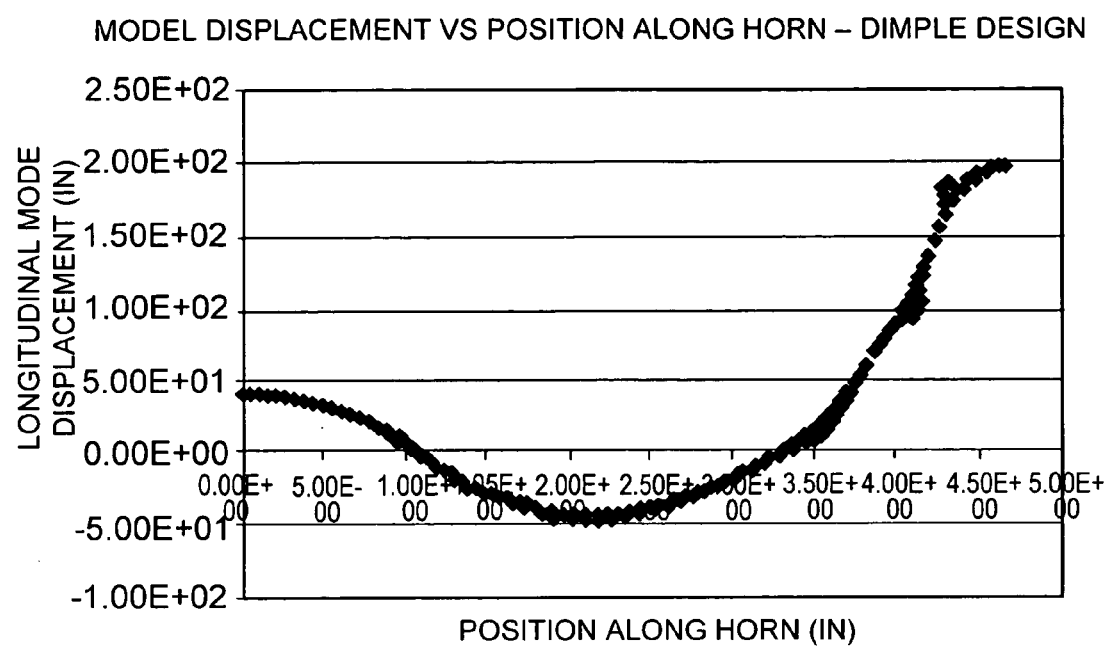

FIGS. 15A through 15C are graphs of the longitudinal mode displacement as a function of the position along acoustic horn assembly 3500a, as modeled using finite element analysis and based on the model shown in FIG. 14. FIG. 15A shows that a first node is located 1.12 inches from proximal end 3505a. FIG. 15B shows that a second node is located 3.28 inches from proximal end 3505a. FIG. 15C shows the longitudinal mode displacement along the entire length of acoustic horn assembly 3500a. As shown in FIG. 15C, acoustic horn assembly 3500a supports a full wavelength along its length. Thus, FIGS. 14 and 15A through 15C show that, based on modeling data, an acoustic horn assembly can be designed that supports a full wavelength along its length, has a first node located at its transducers, and has a second node located where the hand piece body contacts the distal horn.

Other designs can also be modeled using finite element analysis. For example, without wishing to be bound by theory, it is believed that locating a node at the acoustic coupler can adversely affect the propagation of ultrasonic vibrations along the wire. It is therefore believed that it can be desirable for system 1000 to be designed so that a node is not present at the acoustic coupler (whether wire 4000 is bent or unbent). In certain embodiments, an acoustic horn assembly can be configured so that modeling using finite element analysis shows that the acoustic horn assembly supports a node at a first location proximal to, but not at, the acoustic coupler when the wire is unbent, and supports a node at a second location (different from the first location) that is proximal to, but not at, the acoustic coupler when the wire is bent (e.g., when the wire is disposed within a tortuous vessel).

Figure 16:
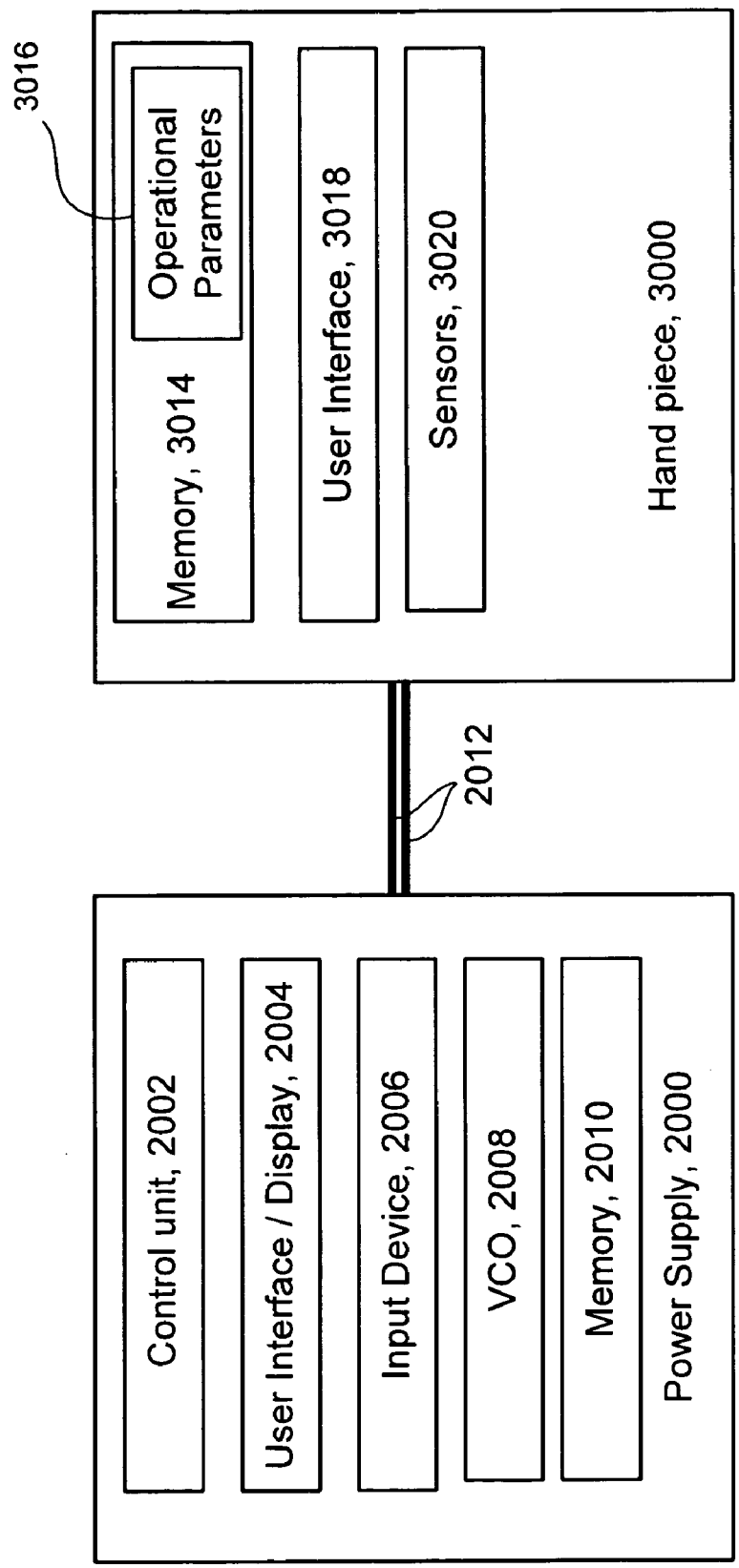
FIG. 16 is a schematic drawing of a portion of an ultrasound vibration system.

As discussed above, power supply 2000 is in electrical communication with hand piece assembly 3000. FIG. 16 shows that power supply 2000 is electrically connected to hand piece assembly 3000 by multi-wire cable 2012 so that power supply 2000 can deliver electrical energy to hand piece assembly 3000. In addition to providing an electrical energy path from power supply 2000 to hand piece assembly 3000, cable 2012 provides a communication path between power supply 2000 and hand piece assembly 3000 so that information (e.g., operational parameters 3016 for system 1000) can be transferred between power supply 2000 and hand piece assembly 3000. For example, in some embodiments, multi-wire cable 2012 includes a first wire for communicating information between hand piece assembly 3000 and power supply 2000 and a second wire for transmitting power from power supply 2000 to hand piece assembly 3000 (e.g., to piezoelectric elements 3520 of acoustic horn assembly 3500 of hand piece assembly 3000). In addition, multi-wire cable 2012 can include a third, ground wire.

Power supply 2000 includes a control unit 2002, a user interface/display 2004, an input device 2006, a voltage controlled oscillator (VCO) 2008, and a memory 2010.

Control unit 2002 monitors and adjusts the operation of ultrasound vibration system 1000 (see discussion below).

User interface/display 2004 provides a visual display on power supply 2000. User interface/display 2004 can display various information, such as instructions for a user, status information (e.g., information that indicates whether the ultrasound vibration system 1000 is on or off, information that indicates whether power is being supplied to hand piece assembly 3000, information that indicates the amount of time left before system 1000 will disable hand piece assembly 3000), operational parameters (e.g., a voltage output of VCO 2008, a current delivered to hand piece assembly 3000, a temperature of acoustic horn assembly 3500, identification information for hand piece assembly 3000, a resonant frequency of acoustic horn assembly 3500, a temperature of wire 4000, a resonant frequency of wire 4000), messages (e.g., a message displaying the company name, a message indicating that a calibration is needed, a message reporting a malfunction, a message indicating a reason for deactivation of hand piece assembly 3000, a message reporting the source of an error in system 1000, a message requesting action or feedback from an operator, a message displaying a current state of system 1000), alarms (e.g., alarms indicating a warning of a failure in the system 1000, such as an alarm indicating that a battery is low, an alarm indicating that the temperature of hand piece assembly 3000 is above a predetermined value, an alarm indicating a maximum activation period of hand piece assembly 3000 has been exceeded, an alarm indicating that a maximum post-activation use period of hand piece assembly 3000 has been exceeded), or combinations thereof.

Input device 2006 allows a user to program or modify certain operational parameters of ultrasound vibration system 1000. Input device 2006 can be, for example, a keyboard, a mouse, a touch screen, one or more control knobs, one or more buttons, one or more switches, or a combination thereof.

VCO 2008 is in electrical communication with hand piece assembly 3000 and provides an oscillating voltage (e.g., a sinusoidal voltage) to hand piece assembly 3000 that causes wire 4000 to vibrate during use. In general, the frequency of the output voltage of VCO 2008 can be changed during use of ultrasound vibration system 1000 to respond to changes in a resonant frequency (e.g., the fundamental resonant frequency or a harmonic of the fundamental resonant frequency) of acoustic horn assembly 3500 of hand piece assembly 3000. For example, an input voltage to VCO 2008 can be changed during use so that the frequency of the output voltage of VCO 2008 remains substantially equal to the resonant frequency of acoustic horn assembly 3500, as discussed in more detail below.

Memory 2010 stores information (e.g., one or more operational parameters) that is used to operate ultrasound vibration system 1000.

Hand piece assembly 3000 includes memory 3014, a user interface 3018, and sensors 3020.

In general, memory 3014 stores information (e.g., one or more operational parameters 3016 for hand piece assembly 3000) that is used to operate ultrasound vibration system 1000. Generally, the information stored in memory 3014 can be user modifiable or non-user modifiable. In some embodiments, some of the information (e.g., one or more of the operational parameters 3016) stored in memory 3014 can be user modifiable, and some of the other information (e.g., one or more of the other operational parameters 3016) stored in memory 3014 can be non-user modifiable. Non-user modifiable information can, for example, be stored in a write-protected portion (e.g., a erasable programmable read-only memory (EPROM) portion) of memory 3014 such that, after this information is initially programmed for hand piece assembly 3000, it can not be changed by an operator. As an example, in some embodiments, one or more of the operational parameters 3016 (e.g., maximum activation period of hand piece assembly 3000, maximum post-activation use period of hand piece assembly 3000, maximum operational temperature for acoustic horn assembly 3500, maximum operational temperature for wire 4000) can be pre-programmed into memory 3014 prior to distributing hand piece assembly 3000 for use (e.g., during manufacture and/or assembly of hand piece assembly 3000).

Examples of operational parameters 3016 include an output voltage of VCO 2008, a current in hand piece assembly 3000, a temperature of one or more components of hand piece assembly 3000, the maximum activation period of hand piece assembly 3000, the maximum post-activation use period of hand piece assembly 3000, a voltage to be applied to VCO 2008, the resonant frequency of acoustic horn assembly 3500 (e.g., as determined during the manufacture of acoustic horn assembly 3500, or as determined during the use of system 1000), the resonant frequency of wire 4000 (e.g., as determined during the manufacture of wire 4000, or as determined during the use of system 1000), a temperature of wire 4000, identification information (e.g., for hand piece assembly 3000, wire 4000, and/or power supply 2000), and a medical procedure to be performed with system 1000 (e.g., ablating occlusions, removing plaque, removing bone cement, treating gynecological tissue, debulking prostate, treating urolithiasis, reinforcing bone, cleaning a vascular access device, treating deep vein thrombosis (DVT), treating peripheral arterial disease, and treating chronic total occlusions, phacoemulsification and/or treating coronary thrombosis lesions).

User interface 3018 can display information that may be useful for the operator during use of system 1000. Examples of such information include one or more operational parameters 3016, one or more messages (see discussion below), or a combination thereof.

Sensors 3020 are generally used to monitor one or more of the operational parameters 3016 (e.g., voltage, current, temperature, stress, strain) of hand piece assembly 3000 (e.g., of acoustic horn assembly 3500 of hand piece assembly 3000) and/or wire 4000 during operation of ultrasound vibration system 1000. Sensors 3020 provide information to power supply 2000 via cable 2012, and, in response, power supply 2000 can modify the operation of hand piece assembly 3000 (e.g., by increasing the frequency of the output voltage of VCO 2008, by decreasing the frequency of the output voltage of VCO 2008). Alternatively or additionally, one or more of operational parameters 3016 can be monitored by power supply 2000. In some embodiments, for example, the voltage and current in hand piece assembly 3000 are monitored by power supply 2000 while the temperature of hand piece assembly 3000 (e.g., air temperature within hand piece assembly 3000) is monitored by sensor 3020 in hand piece assembly 3000.

Figure 17:
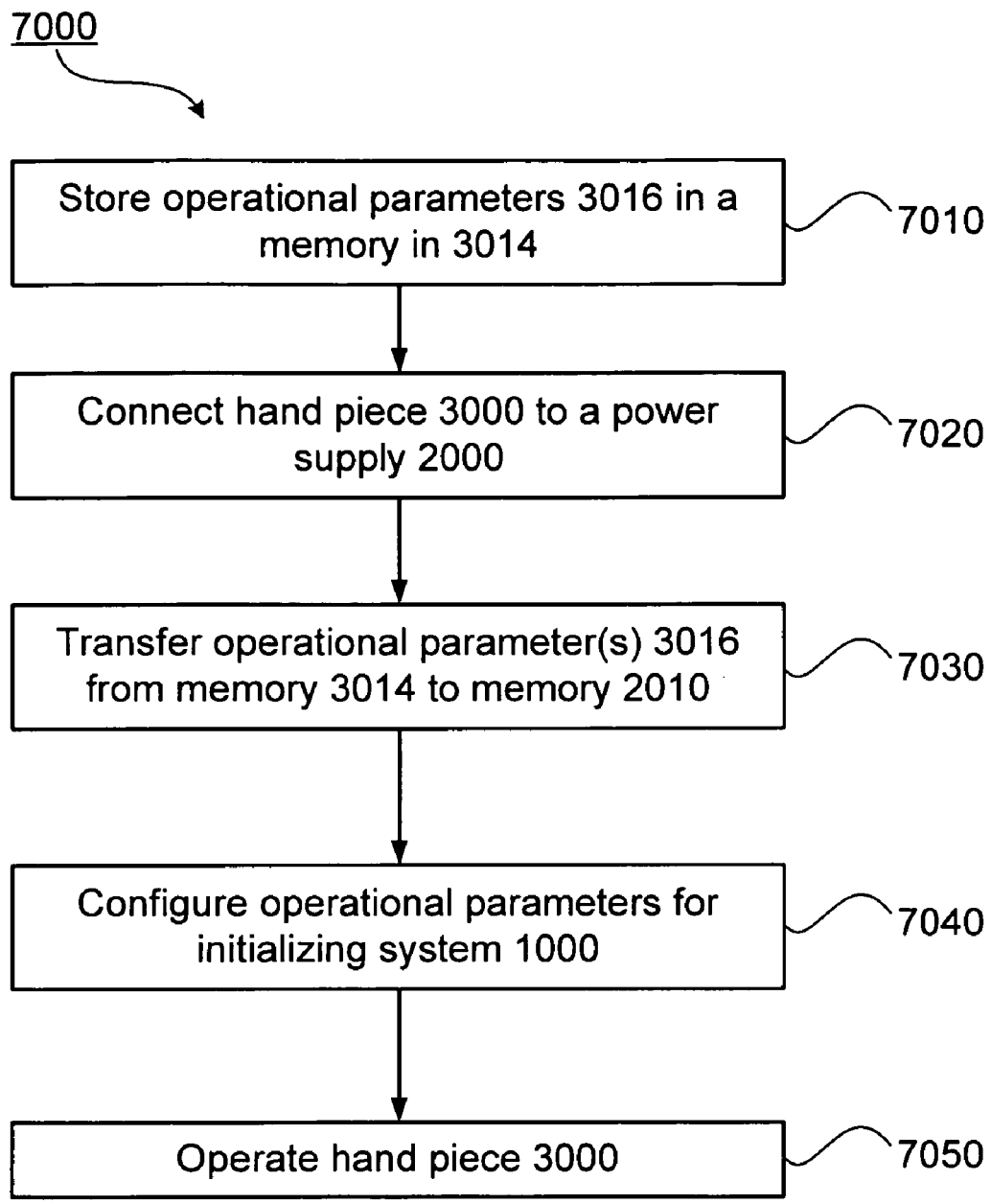
FIG. 17 is a flow chart of an initialization and activation/operation process for an ultrasound vibration system.

FIG. 17 is a flow chart of an exemplary initialization and activation/operation process 7000 for system 1000. Operational parameters 3016 are stored in memory 3014 of hand piece assembly 3000 (7010). Hand piece assembly 3000 is connected to power supply 2000 (7020), and one or more of the operational parameters 3016 are transferred from memory 3014 to memory 2010 (7030). Based on the operational parameter(s) 3016 transferred to memory 2010, power supply 2000 configures the operational parameter(s) (e.g., the amplitude of the output voltage of VCO 2008) for initializing system 1000 (7040). Operational parameters 3016 can also include a frequency range used to sweep the output frequency of VCO 2008 to determine a resonant frequency of acoustic horn assembly 3500. Based on operational parameters 3016, an initial frequency sweep and tuning procedure is performed to configure the frequency of the output voltage of VCO 2008 for initializing system 1000. After initializing system 1000, power supply 2000 generates a voltage signal that is transferred to hand piece assembly 3000 to activate and/or operate hand piece assembly 3000 (7050).

Acoustic horn assembly 3500 can be designed to vibrate in a longitudinal vibration mode. Acoustic horn assembly 3500 can vibrationally resonate at its fundamental resonant frequency and at harmonics of its fundamental resonant frequency. Exciting acoustic horn assembly 3500 at its resonant frequency (e.g., at its fundamental resonant frequency or at a harmonic of its fundamental resonant frequency) can increase the efficacy of converting an electrical input signal to vibration amplitude at the distal end of acoustic horn assembly 3500 where acoustic coupler 1700 is located. The particular mode and harmonic frequency of excitation or vibration of acoustic horn assembly 3500 is generally determined by design and can be selected based on the intended use of system 1000. The particular mode and harmonic frequency of excitation or vibration of acoustic horn assembly 3500 can, for example, be selected based on the desired mode and frequency of the attached wire 4000. In some embodiments, system 1000 is configured so that, during use, acoustic horn assembly 3500 vibrates in a longitudinal mode at the second harmonic of its fundamental resonant frequency. However, acoustic horn assembly 3500 can be designed to vibrate in other modes and/or at other harmonic frequencies, depending on the intended use of system 1000.

In general, the resonant frequency (e.g., the fundamental resonant frequency or a harmonic of the fundamental resonant frequency) of acoustic horn assembly 3500 depends upon a number of parameters, some of which may be relatively constant during use of system 1000 and some of which may change a substantial amount during use of system 1000. Typically, the resonant frequency of acoustic horn assembly 3500 depends on one or more physical properties (e.g., length, cross sectional shape, cross sectional area) of acoustic horn assembly 3500 and/or one or more material properties (e.g., yield strength, material modulus) of acoustic horn assembly 3500. Generally, the resonant frequency of acoustic horn assembly 3500 also depends on the temperature of acoustic horn assembly 3500. As an example, as the temperature of acoustic horn assembly 3500 increases, the resonant frequency of acoustic horn assembly 3500 can decrease. As another example as the temperature of acoustic horn assembly 3500 decreases, the resonant frequency of acoustic horn assembly 3500 can increase. Thus, it is generally desirable for power supply 2000 to be capable of modifying the frequency of the output voltage of VCO 2008 to hand piece assembly 3000 so that, as the resonant frequency of acoustic horn assembly 3500 changes, the frequency of the output voltage of VCO 2008 also changes to be at about the same frequency as (e.g., identical to) the resonant frequency of acoustic horn assembly 3500.

In some embodiments, the resonant frequency of acoustic horn assembly 3500 ranges from about ten kHz to about 80 kHz (e.g., about 20 kHz to about 60 kHz, about 40 kHz to about 60 kHz, about 40 kHz).

Wire 4000 can be designed to vibrate in a longitudinal vibration mode. Wire 4000 can vibrate at its resonant frequency (e.g., at its fundamental resonant frequency or at a harmonic of its fundamental resonant frequency) or at frequencies other than its resonant frequency. The resonant frequency of wire 4000 generally depends upon a number of parameters, some of which may be relatively constant during use of system 1000 and some of which may change a substantial amount during use of system 1000. Typically, the resonant frequency of wire 4000 depends on one or more physical properties (e.g., length, cross sectional shape, cross sectional area) of wire 4000 and/or one or more material properties (e.g., yield strength, material modulus) of wire 4000. Generally, the resonant frequency of wire 4000 also depends on the temperature of wire 4000 and/or the mechanical loading of wire 4000 (e.g., the degree to which wire 4000 is bent). As an example, as the temperature of wire 4000 increases, the resonant frequency of wire 4000 can make a corresponding change. As another example as the temperature of wire 4000 decreases, the resonant frequency of wire 4000 can make a corresponding change.

In certain embodiments, the longitudinal resonant frequency (e.g., the fundamental longitudinal resonant frequency or a harmonic of the fundamental longitudinal resonant frequency) of acoustic horn assembly 3500 differs from the longitudinal resonant frequency (e.g., the fundamental longitudinal resonant frequency or a harmonic of the fundamental longitudinal resonant frequency) of wire 4000. The longitudinal resonant frequency of acoustic horn assembly 3500 can, for example, differ from the nearest longitudinal resonant frequency of wire 4000 by about one kHz to about six kHz (e.g., about three kHz). Wire 4000 and acoustic horn assembly 3500 can, for example, be designed such that their respective longitudinal resonant frequencies differ from one another throughout use of system 1000. Maintaining a difference between the longitudinal resonant frequencies of wire 4000 and acoustic horn assembly 3500 can help power supply 2000 to lock onto the longitudinal resonant frequency of acoustic horn assembly 3500 during use. The difference between the longitudinal resonant frequencies of wire 4000 and acoustic horn assembly 3500 can, for example, help to provide a measurable phase difference between the voltage and current delivered to acoustic horn assembly 3500 by power supply 2000 to help power supply 2000 lock onto the longitudinal resonant frequency of acoustic horn assembly 3500 during use.

In certain embodiments, ultrasound horn assembly 3500 has a longitudinal fundamental resonant frequency of about 20 kHz and wire 4000 has a fundamental resonant frequency of about 2 kHz. In such embodiments, during use, ultrasound horn assembly 3500 can be excited at 40 kHz, which is the second harmonic of its fundamental longitudinal resonant frequency. The vibration of acoustic horn assembly 3500 can cause wire 4000 to be excited or vibrated at 40 kHz. In some embodiments this is a frequency that lies between the ninth and tenth harmonics of the fundamental longitudinal resonant frequency of wire 4000. This frequency can alternatively fall between the $19^{th}$ and $20^{th}$ or $24^{th}$ and $25^{th}$ harmonics of the fundamental longitudinal resonant frequency of wire 4000. Because wire 4000 is excited at a frequency between harmonics of its longitudinal resonant frequency, wire 4000 does not vibrate at its resonant frequency.

Figure 18:
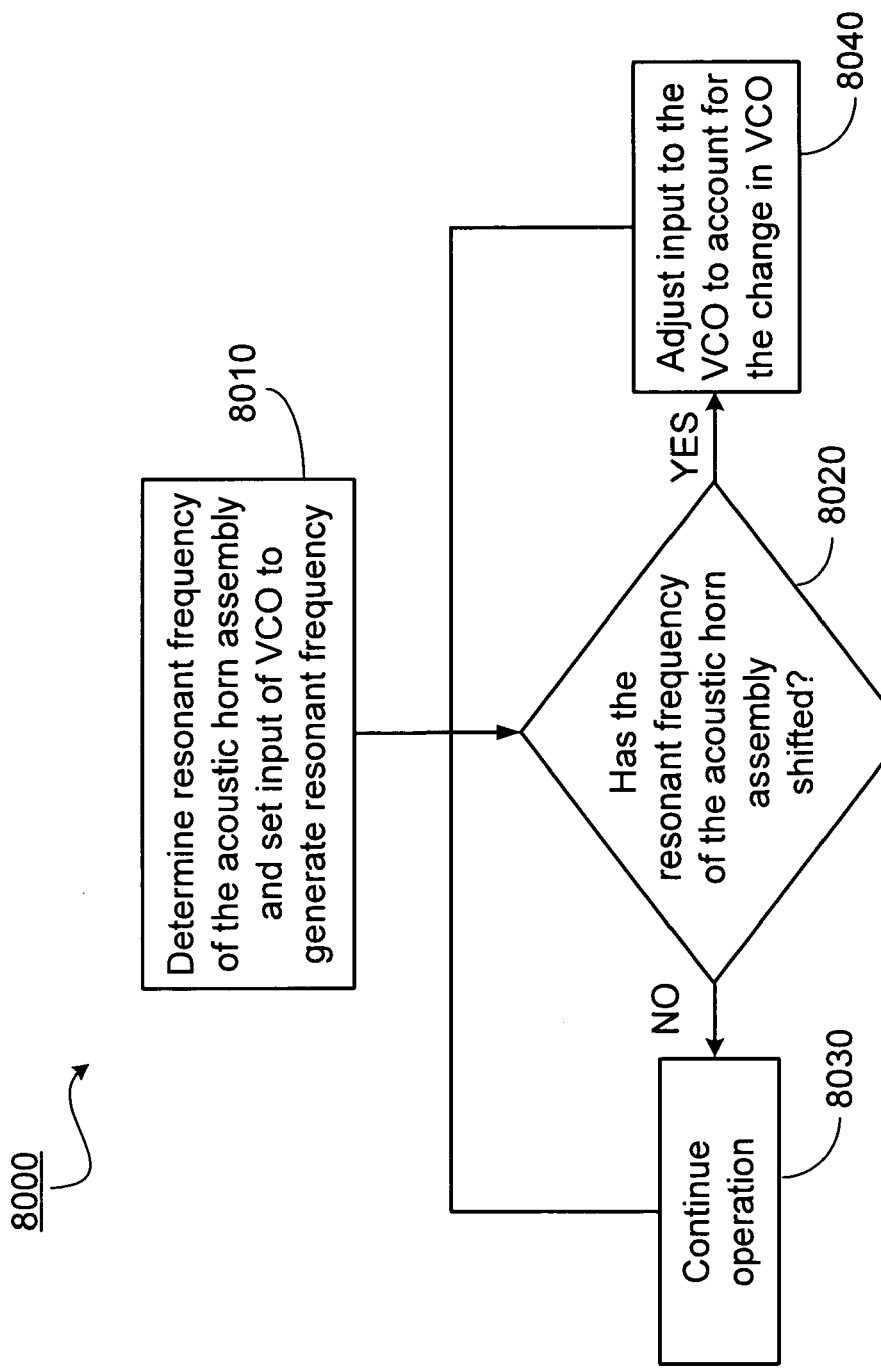
FIG. 18 is a flow chart of a process for modifying the vibrational frequency of an acoustic assembly of a handpiece during use of an ultrasound vibration system.

FIG. 18 is a flow chart of an exemplary process 8000 for modifying the vibrational frequency of acoustic horn assembly 3500 as the resonant frequency of acoustic horn assembly 3500 changes. Power supply 2000 initially determines the resonant frequency of acoustic horn assembly 3500, and power supply 2000 sets VCO 2008 to generate an output voltage at a frequency such that acoustic horn assembly 3500 vibrates at a frequency that is about the same as (e.g., identical to) the resonant frequency of acoustic horn assembly 3500 (8010). As ultrasound vibration system 1000 is being used, power supply 2000 determines if the resonant frequency of acoustic horn assembly 3500 has changed (8020). If the resonant frequency of acoustic horn assembly 3500 has not changed, power supply 2000 continues to supply the same input voltage to VCO 2008, causing VCO 2008 to provide the same output voltage (e.g., a voltage having the same frequency) to acoustic horn assembly 3500 (8030). If the resonant frequency of acoustic horn assembly 3500 has changed, power supply 2000 adjusts the input voltage to VCO 2008, changing the frequency of the output voltage of VCO 2008 such that acoustic horn assembly 3500 vibrates at a frequency that is about the same as (e.g., identical to) the new resonant frequency of acoustic horn assembly 3500 (8040). As an example, in some embodiments in which the resonant frequency of acoustic horn assembly 3500 decreases during use of system 1000, power supply 2000 can decrease the frequency of the output voltage of VCO 2008. As another example, in certain embodiments in which the resonant frequency of acoustic horn assembly 3500 increases during use of system 1000, power supply 2000 can increase the frequency of the output voltage of VCO 2008.

In general, power supply 2000 can determine the resonant frequency of acoustic horn assembly 3500 using any desired method or combination of methods. In some embodiments, power supply 2000 determines the resonant frequency of acoustic horn assembly 3500 based on the phase difference between the voltage in acoustic horn assembly 3500 and the current in acoustic horn assembly 3500. Typically, power supply 2000 determines the voltage in acoustic horn assembly 3500 and the current in acoustic horn assembly 3500 via one or more current and voltage sensing devices.

Figure 19:
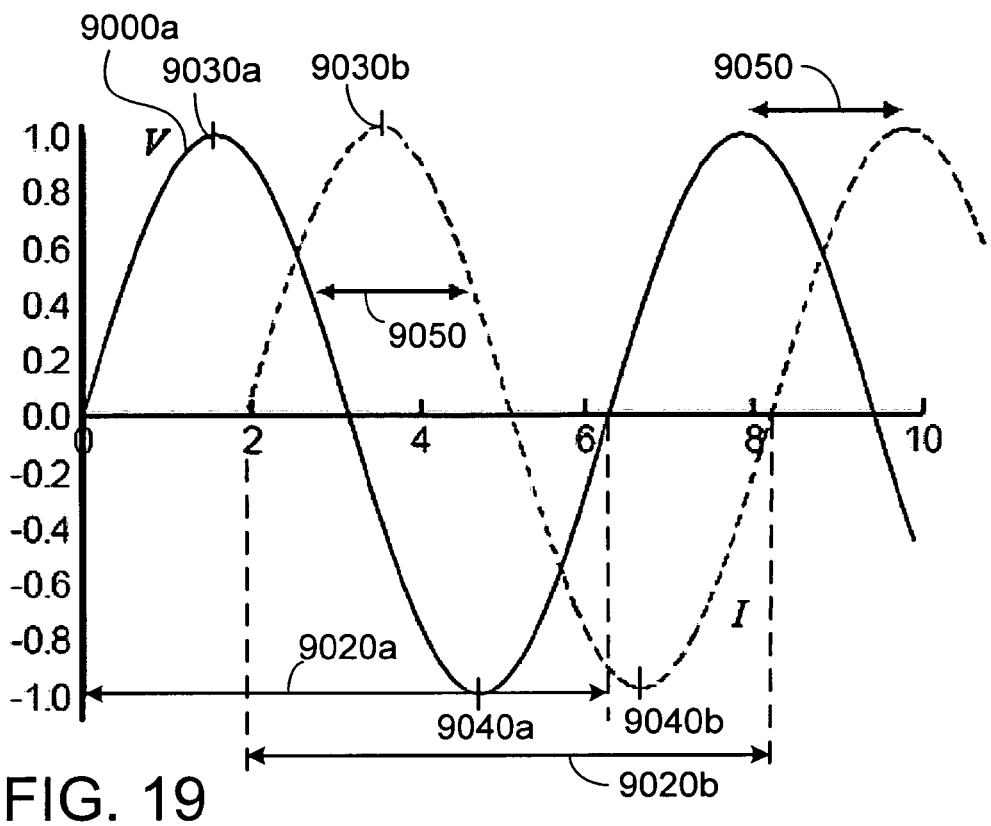
FIG. 19 is a graph of a voltage signal and a current signal where the phase difference between the signals is non-zero.
Figure 20:
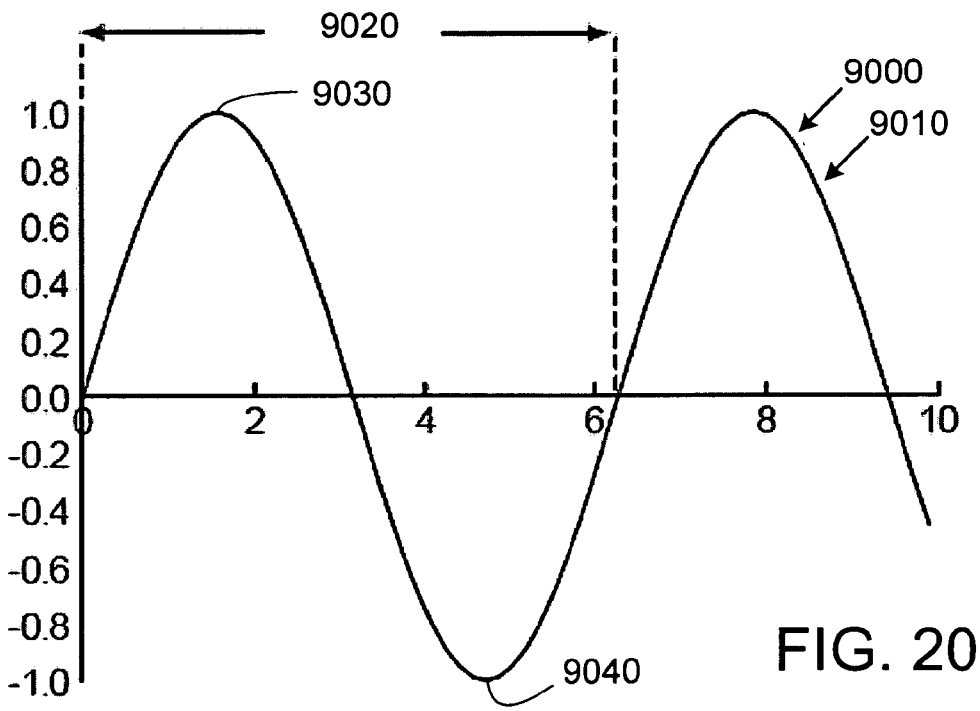
FIG. 20 is a graph of a voltage signal and a current signal where the phase difference between the signals is zero.

FIG. 19 shows a graph of a voltage signal 9000a and a current signal 9010a where a phase difference 9050 between these signals is non-zero, and FIG. 20 shows a graph of a voltage signal 9000 and a current signal 9010 where the phase difference between these signals is zero. In FIG. 19, voltage signal 9000a has a period 9020a, a maximum value 9030a, and a minimum value 9040a, and current signal 9010a has a period 9020b, a maximum value 9030b, and a minimum value 9040b. In FIG. 20, both voltage signal 9000 and current signal 9010 have a period 9020, a maximum value 9030 and a minimum value 9040.

During use of system 1000, power supply 2000 monitors both the voltage in acoustic horn assembly 3500 and the current in acoustic horn assembly 3500 to determine the size of the phase difference between these signals. If the phase difference is zero, power supply 2000 does not change the frequency of the output voltage of VCO 2008. However, if the phase difference is non-zero, power supply 2000 changes the frequency of the output voltage of VCO 2008 so that acoustic horn assembly 3500 vibrates at a frequency that is about the same as (e.g., identical to) the resonant frequency of acoustic horn assembly 3500.

Figure 21:
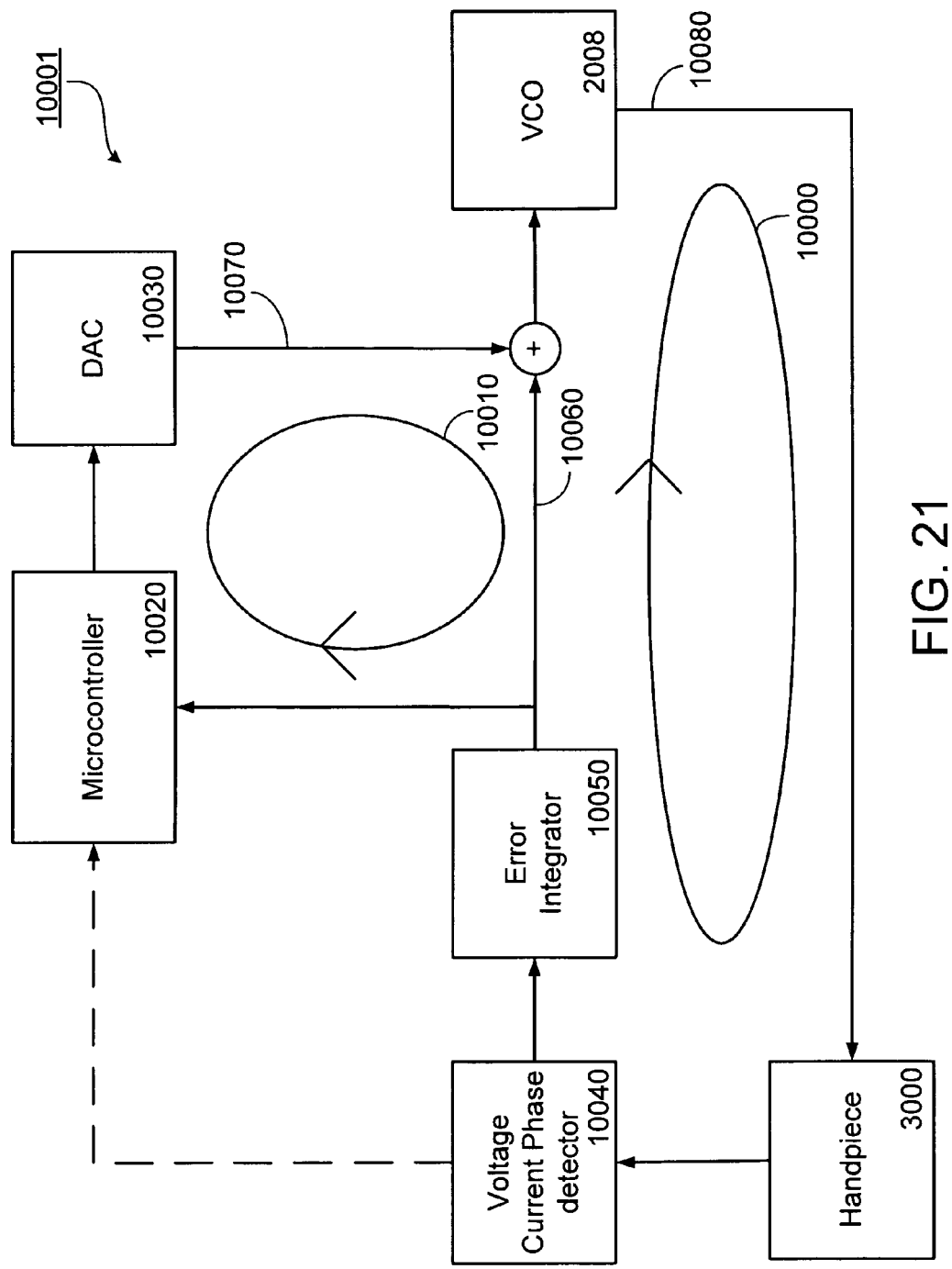
FIG. 21 is a block diagram of a system designed to adjust the vibrational frequency of an acoustic assembly of a handpiece during use of an ultrasound vibration system.

FIG. 21 shows a block diagram of an exemplary control unit 10001 designed to monitor the voltage in acoustic horn assembly 3500 and the current in acoustic horn assembly 3500, and to modify the frequency of the output voltage of VCO 2008 so that, during use of system 1000, the vibrational frequency of acoustic horn assembly 3500 can be adjusted to be about the same as (e.g., identical to) the resonant frequency of acoustic horn assembly 3500.

Control unit 10001 includes an analog control loop 10000 and a digital control loop 10010. Analog control loop 10000 produces a voltage 10060 that is based on the phase difference between the voltage in acoustic horn assembly 3500 and the current in acoustic horn assembly 3500. Voltage 10060 acts as an input voltage to VCO 2008. Similarly, digital control loop 10010 produces a voltage 10070 that is based on the phase difference between the voltage in acoustic horn assembly 3500 and the current in acoustic horn assembly 3500, and voltage 10070 acts as an input to voltage VCO 2008. By providing respective input voltages to VCO 2008, analog control loop 10000 and digital control loop 10010 determine the frequency of the output voltage of VCO 2008.

Voltage 10060 has a maximum range that is predetermined (e.g., set in memory) based on the expected range for the resonant frequency of acoustic horn assembly 3500 during use of system 1000, and voltage 10070 has a maximum range that is predetermined (e.g., set in memory) based on the expected range for the resonant frequency of acoustic horn assembly 3500 during use of system 1000. As a result, the maximum amount by which analog control loop 10000 can adjust the frequency of the output voltage of VCO 2008 is predetermined, and the maximum amount by which digital control loop 10010 can adjust the frequency of the output voltage of VCO 2008 is predetermined. In general, the maximum range of voltage 10070 is greater than the maximum range of voltage 10060. With this arrangement, digital control loop 10010 sets a center frequency for the output voltage of VCO 2008, and analog loop 10000 then dynamically implements deviations in the frequency of the output voltage of VCO 2008 about this center frequency (e.g., within about 200 Hz of the center frequency, within about 100 Hz of the center frequency, within about 50 Hz of the center frequency, within about 10 Hz of the center frequency) to maintain a desired phase difference (e.g., about zero phase difference) between the current in hand piece assembly 3000 and the voltage in hand piece assembly 3000.

Analog control loop 10000 establishes the value of voltage 10060 as follows. A voltage current phase detector 10040 is placed in electrical communication with hand piece assembly 3000, and phase detector 10040 determines the phase difference between the voltage applied to acoustic horn assembly 3500 and the resulting current in acoustic horn assembly 3500. Phase detector 10040 provides to error integrator 10050 a signal that corresponds to the phase difference between the voltage in acoustic horn assembly 3500 and the current in acoustic horn assembly 3500. Error integrator 10050 produces voltage 10060 based on the signal received from phase detector 10040. Generally, the magnitude of voltage 10060 is proportional to the magnitude of the phase difference between the current in acoustic horn assembly 3500 and the voltage in acoustic horn assembly 3500. In other words, if the phase difference is relatively small amount, the magnitude of voltage 10060 is usually relatively small, and, if the phase difference is relatively large, the magnitude of voltage 10060 is usually relatively large. In general, integrator 10050 is biased such that error integrator 10050 changes voltage 10060 only when the phase difference between the voltage in acoustic horn assembly 3500 and the current in acoustic horn assembly 3500 is outside a predetermined range. For example, phase error integrator 10050 can be configured to change voltage 10060 only when the absolute value of the phase difference between the voltage in hand piece assembly 3000 and the current in hand piece assembly 3000 is greater than about 5° (e.g., greater than about 10°, greater than about 15°, greater than about 20°). Typically, if the resonant frequency of acoustic horn assembly 3500 decreases, error integrator 10050 changes the value of voltage 10060 to decrease the frequency of the output voltage of VCO 2008, and, if the resonant frequency of acoustic horn assembly 3500 increases, error integrator 10050 changes voltage 10060 to increase the frequency of the output voltage of VCO 2008. In general, error integrator 10050 can use any appropriate method to produce voltage 10060 based on the signal received from phase detector 10040. As an example, in some embodiments, error integrator 10050 can include a look-up table that informs error integrator 10050 of the appropriate value for voltage 10060 based on the signal error integrator 10050 receives from phase detector 10040.

Digital control loop 10010 establishes the value of voltage 10070 as follows. During initialization of system 1000, the signal produced by phase detector 10040 is the input signal for microcontroller 10020, and during operation of system 1000 the signal produced by error integrator 10050 is the input signal for microcontroller 10020. Based on the input signal it receives, microcontroller 10020 sends a digital signal to analog to DAC 10030. DAC 10030 converts the digital signal it receives from microcontroller 10020 to an analog signal, which is voltage 10070. Thus, microcontroller 10020 uses the signal it receives from phase detector 10040, which corresponds to the phase difference between the voltage in acoustic horn assembly 3500 and the current in acoustic horn assembly 3500, to determine the signal it should send to DAC 10030 so that voltage 10070 is changed in a manner that achieves the desired corresponding change in the frequency of the output voltage of VCO 2008. Microcontroller 10020 can do this, for example, based on the maximum range of the change in the frequency of the output voltage of VCO 2008 that voltage 10070 can make. Typically, microcontroller 10020 sends a signal to DAC 10030 so that DAC 10030 changes voltage 10070 in the appropriate direction (e.g., decreasing voltage 10070 if the phase difference between the voltage in acoustic horn assembly 3500 and the current in acoustic horn assembly 3500 is negative, increasing voltage 10070 if the phase difference between the voltage in acoustic horn assembly 3500 and the current in acoustic horn assembly 3500 is positive) and by an absolute value that is proportional to the magnitude of the phase difference between the voltage in acoustic horn assembly 3500 and the current in acoustic horn assembly 3500.

Figure 22:
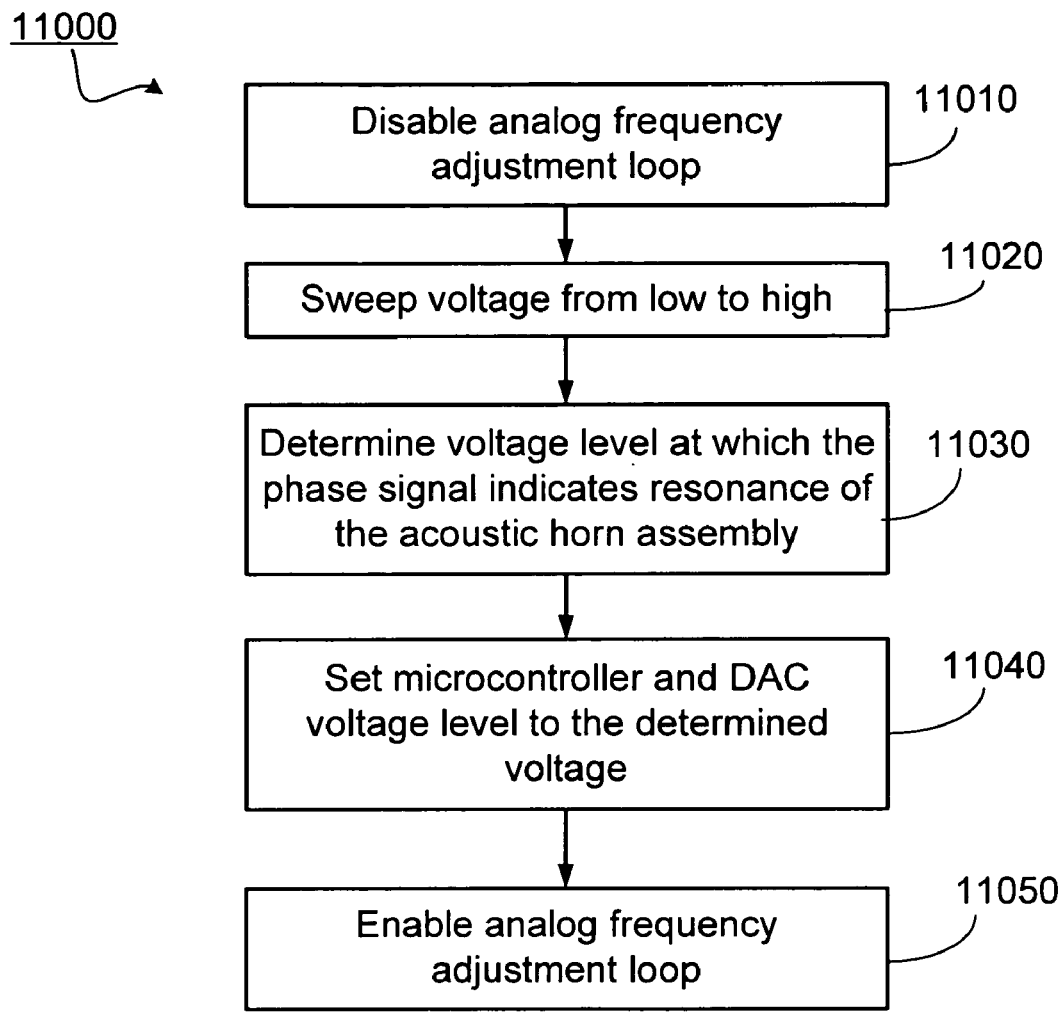
FIG. 22 shows a process for determining the initial center frequency for the output voltage of a voltage controlled oscillator.

FIG. 22 shows a process 11000 for determining the initial center frequency for the output voltage of VCO 2008. Power supply 2000 disables analog control loop 10000 (11010). This causes voltage 10060 to be zero volts, and so the frequency of the output voltage of VCO 2008 is determined by output voltage 10070 of digital control loop 10010. While analog control loop 10010 is disabled, the output signal from phase detector 10040 is the input signal for microcontroller 10020. The amplitude of voltage 10070 is swept through its maximum range (11020), causing the frequency of voltage 10080 to be swept through its maximum frequency range. As the amplitude of voltage 10070 is swept through its maximum range, phase detector 10040 monitors the phase difference between the voltage in acoustic horn assembly 3500 and the current in acoustic horn assembly 3500, and provides this information to microcontroller 10020. Microcontroller 10020 then determines the frequency for the output voltage of VCO 2008 that results in the smallest phase difference and will cause acoustic horn assembly 3500 to vibrate at a frequency that is about the same as (e.g., identical to) the resonant frequency of acoustic horn assembly 3500 (11030). Microcontroller 10020 then provides the appropriate digital signal to DAC 10030, and DAC 10030 converts this signal to an analog signal (voltage 10070) so that the frequency of the output voltage of VCO 2008 results in acoustic horn assembly 3500 vibrating at a frequency that is about the same as (e.g., identical to) the resonant frequency of acoustic horn assembly 3500 (11040). Power supply 2000 subsequently enables analog control loop 10000 (11050), and digital control loop 10010 and analog control loop 10000 are used to dynamically adjust the output frequency of VCO 2008 via the amplitude of voltages 10060 and 10070 applied to VCO 2008, as discussed above.

During operation of system 1000, the output of error integrator 10050 (i.e., voltage 10060) is the input to digital control loop 10010. As a result, the output of analog control loop 10000 (i.e., voltage 10060) determines the output of digital control loop 10010 (i.e., voltage 10070). Thus, digital control loop 10010 dynamically changes the center frequency of the output voltage of VCO 2008 based on voltage 10600, which, in turn, is based on the phase difference between the voltage in acoustic horn assembly 3500 and the current in acoustic horn assembly 3500.

Figure 23:
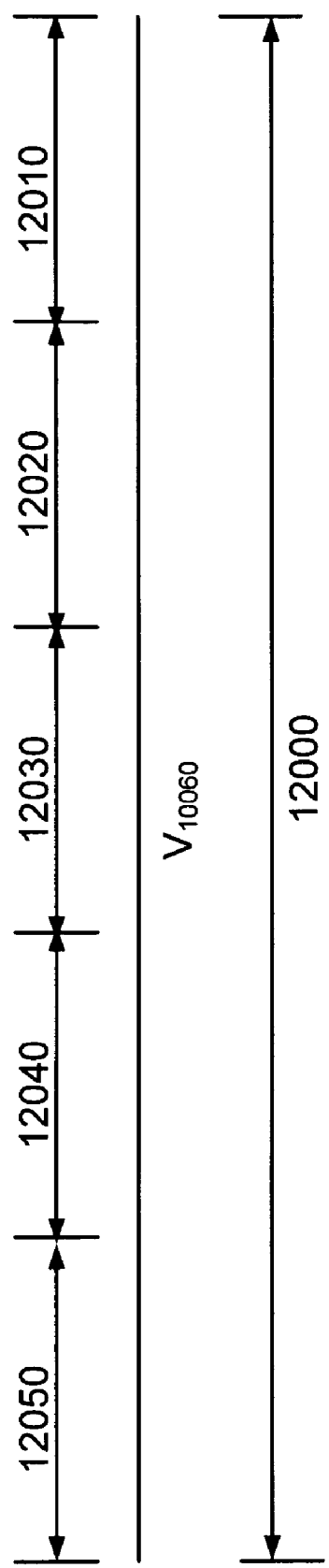
FIG. 23 shows a maximum range of values for an input voltage for a voltage controlled oscillator.

As noted above, there is a predetermined maximum range of values for voltage 10060. This maximum range of values for voltage 10060 can be divided into multiple regions so that the amount by which voltage 10060 causes digital control loop 10010 to change the frequency of the output voltage of VCO 2008 depends on the region in which voltage 10060 is located. For example, FIG. 23 shows a maximum range 12000 of values for voltage 10060. Range 12000 is divided into regions 12010, 12020, 12030, 12040 12050. When voltage 10060 is in region 12030, voltage 10060 causes relatively little or no change in the frequency of the output voltage of VCO 2008. When voltage 10060 is in region 12010, voltage 10060 causes its maximum positive change in the frequency of the output voltage of VCO 2008, and, when voltage 10060 is in region 12050, voltage 10060 causes its maximum negative change in the frequency of the output voltage of VCO 2008. When voltage 10060 is in region 12020, voltage 10600 causes a positive change in the frequency of the output voltage of VCO 2008 that is greater than that caused when voltage 10060 is in region 12030 but less than when voltage 10060 is in region 12010. When voltage 10060 is in region 12040, voltage 10060 causes a negative change in the frequency of the output voltage of VCO 2008 that is greater than that caused when voltage 10060 is in region 12030 but less than when voltage 10060 is in region 12050.

In general, the magnitude of regions 12010, 12020, 12030, 12040, 12050 can be selected as desired. For example, in some embodiments, these regions can have the following magnitudes. Region 12030 can be centered at the middle of range 12000, and region 12030 can occupy at most about 70% (e.g., at most about 60%, at most about 50%, at most about 40%) of range 12000. Region 12020 can have a minimum value corresponding to the maximum value of region 12030, and can occupy at most about 30% (e.g., at most about 25%, at most about 20%, at most about 15%) of range 12000. Region 12040 can have a maximum value corresponding to the minimum value of region 12030, and can occupy at most about 30% (e.g., at most about 25%, at most about 20%, at most about 15%) of range 12000. Region 12010 can have a minimum value corresponding to the maximum value of region 12020 and a maximum value corresponding to the maximum value of voltage 10060. Region 12010 can occupy at most about 10% (e.g., at most about 7%, at most about 5%, at most about 3%) of range 12000. Region 12050 can have a maximum value corresponding to the minimum value of region 12040 and a minimum value corresponding to the minimum value of voltage 10060. Region 12050 can occupy at most about 10% (e.g., at most about 7%, at most about 5%, at most about 3%) of range 12000.

Figure 24:
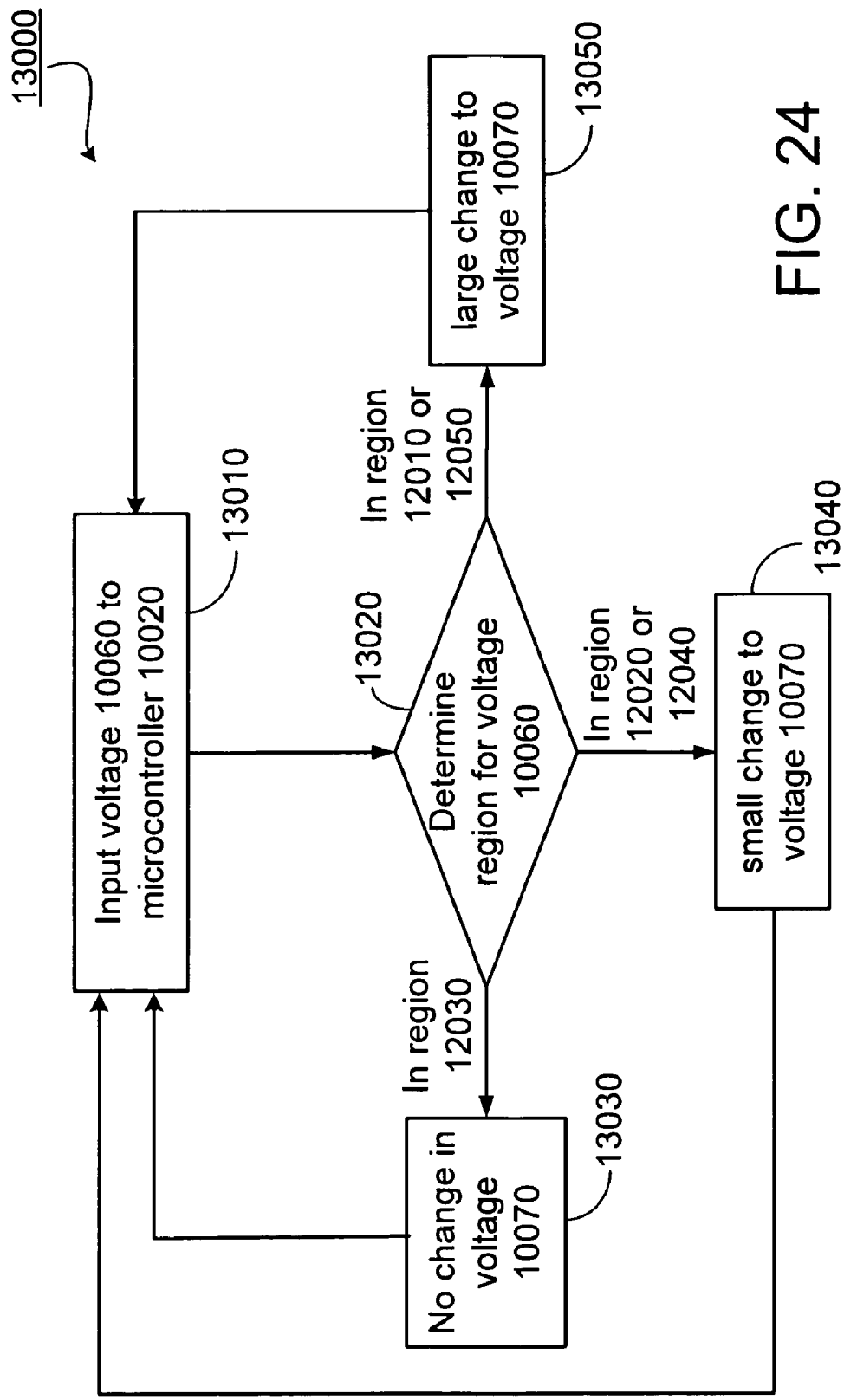
FIG. 24 is a flow chart of a process for modifying the center frequency of the output voltage of a voltage controlled oscillator.

FIG. 24 shows a flow chart of an exemplary process 13000 for modifying the center frequency of the output voltage of VCO 2008 based on the magnitude of voltage 10060, using regions 12010, 12020, 12030, 12040 and 12050 of maximum range 12000 for voltage 10060. First, voltage 10060 is input to microcontroller 10020 (13010). Microcontroller 10020 determines the region in which voltage 10060 is located (13020). If voltage 10060 is in region 12030, microcontroller 10020 sends a signal to DAC 10030 so that voltage 10070 does not change, resulting in no change in the center frequency of the output voltage of VCO 2008 (13030). If voltage 10060 is in region 12020 or region 12040, microcontroller 10020 sends a signal to DAC 10030 so that voltage 10070 changes but by a relatively small amount (13040). This causes the center frequency of the output voltage of VCO 2008 to change but by a relatively small amount, corresponding to a relatively slow change (e.g., as measured in Hz per second) in the center frequency of the output voltage of VCO 2008. For example, voltage 10070 can be adjusted in relatively small frequency increments such that the change in the center frequency of the output voltage of VCO 2008 is relatively slow. If voltage 10060 is in region 12010 or region 12050, microcontroller 10020 sends a signal to DAC 10030 so that voltage 10070 changes by a relatively large amount (13050). This causes the center frequency of the output voltage of VCO 2008 to change by a relatively large amount, corresponding to a relatively fast change (e.g., as measured in Hz per second) in the center frequency of the output voltage of VCO 2008. For example, voltage 10070 can be adjusted in relatively large frequency increments such that the change in center frequency of the output voltage VCO 2008 is relatively fast.

In general, for a given region of voltage 10060, the amount by which voltage 10070 changes is based on the desired change in the frequency of the output voltage of VCO 2008 for the region of voltage 10060, bearing in mind that, because voltage 10070 has a maximum range of values, there is also a corresponding maximum range of change in the frequency of the output voltage of VCO 2008 that can be caused by voltage 10070. As an example, if voltage 10060 is in region 12010 or 12050, then microcontroller 10020 can send a signal to DAC 10030 so that voltage 10070 results in a change in the frequency of the output voltage of VCO 2008 that is from about 25% to about 50% of the maximum range of change in the frequency of the output voltage of VCO 2008 that can be caused by voltage 10070. As another example, if voltage 10060 is in region 12020 or 12040, then microcontroller 10020 can send a signal to DAC 10030 so that voltage 10070 results in a change in the frequency of the output voltage of VCO 2008 that is from at most about 1% (e.g., about 0.5) of the maximum range of change in the frequency of the output voltage of VCO 2008 that can be caused by voltage 10070.

In some embodiments, if certain conditions are satisfied, it may be desirable to be able to prevent hand piece assembly 3000 from being initially enabled and/or to disable hand piece assembly 3000 after it has been initially enabled. As an example, in embodiments in which hand piece assembly 3000 has a maximum time period for which it can be activated (maximum activation period), hand piece assembly 3000 can be disabled if it has met or exceeded this time period. As another example, in embodiments in which hand piece assembly 3000 has a maximum period time after activation that it can be used (maximum post-activation use period), hand piece assembly 3000 can be disabled if it has met or exceeded this time period. As a further example, in embodiments in which acoustic horn assembly 3500 has a temperature that it should not exceed during use of system 1000, hand piece assembly 3000 can be disabled if acoustic horn assembly 3500 is at or above this temperature. As another example, in embodiments in which wire 4000 has a temperature that it should not exceed during use of system 1000, hand piece assembly 3000 can be disabled if wire 4000 is at or above this temperature. As an additional example, in embodiments in which there is a maximum frequency difference that should exist between the vibrational frequency of acoustic horn assembly 3500 and the resonant frequency of acoustic horn assembly 3500, hand piece assembly 3000 can be disabled if this maximum frequency difference is met or exceeded. In some embodiments, if it is determined that hand piece assembly 3000 should be disabled, hand piece assembly 3000 is permanently disabled. In certain embodiments, if it is determined that hand piece assembly 3000 should be disabled, hand piece assembly 3000 is temporarily disabled.

Figure 25:
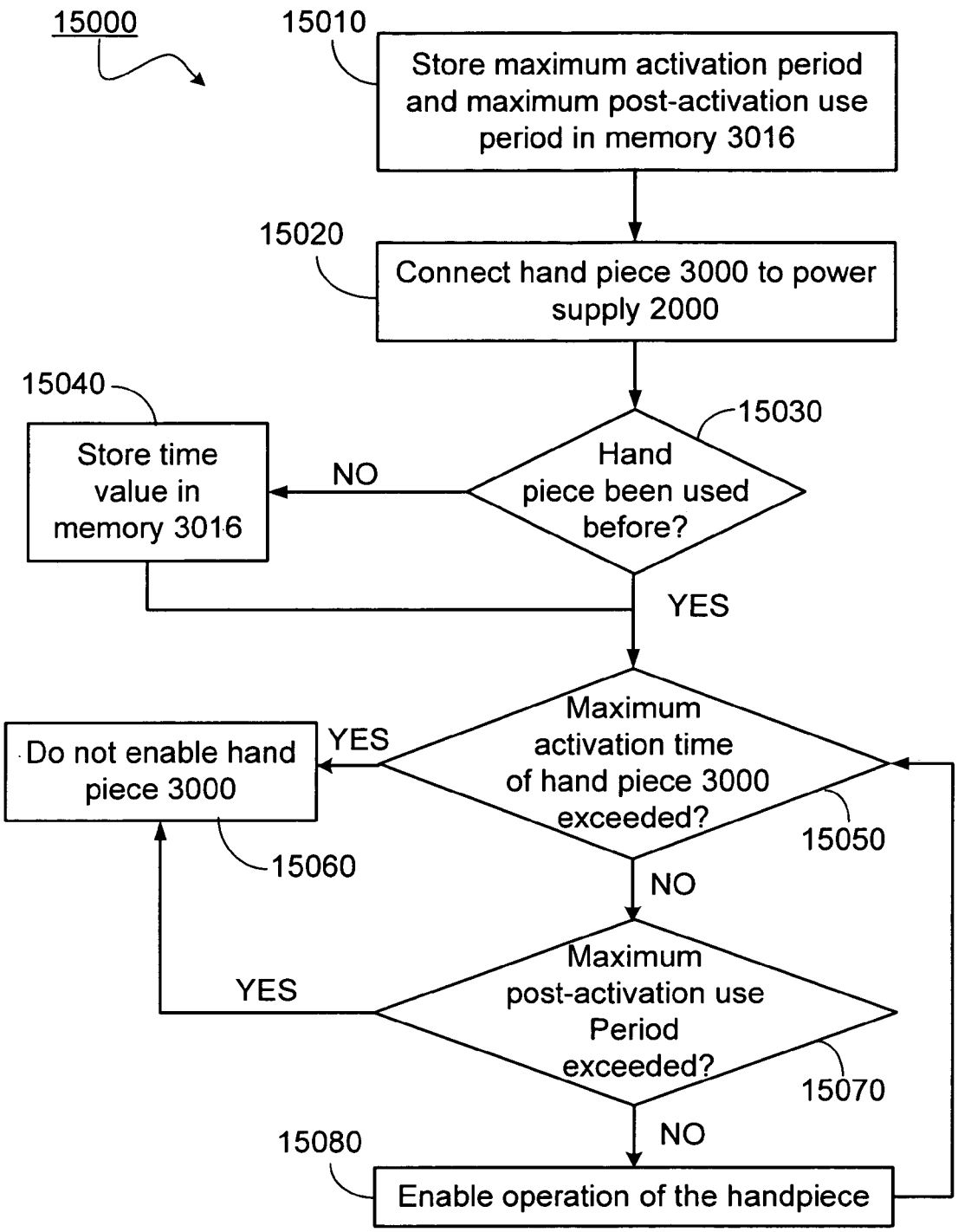
FIG. 25 shows an exemplary process for enabling/disabling a hand piece assembly.

FIG. 25 shows an exemplary process 15000 for enabling hand piece assembly 3000 and subsequently disabling hand piece assembly 3000 where hand piece assembly 3000 has both a maximum activation period and a maximum post-activation use period. The value of the maximum activation period and the value of the maximum post-activation are stored in memory 3014 in hand piece assembly 3000 (15010). In general, the maximum activation period and the maximum post-activation use period can be selected as desired. In some embodiments, the maximum activation period of hand piece assembly 3000 is at most about 10 hours (e.g., at most about five hours, at most about two hours, at most about one hour, at most about 30 minutes, at most about 25 minutes, at most about 20 minutes, at most about 15 minutes, at most about 10 minutes, at most about five minutes). In certain embodiments, the maximum post-activation use period of hand piece assembly 3000 is at most about one week (e.g., at most about five days, at most about two days, at most about one day, at most about 12 hours). Hand piece assembly 3000 is connected to power supply 2000 (15020), and system 1000 determines if hand piece assembly 3000 has been used previously (15030). If hand piece assembly 3000 has not been used before (i.e., hand piece assembly 3000 is being activated for the first time), system 1000 stores in memory 3014 a value indicating the time the hand piece assembly is first activated (15040). System 1000 then compares the amount of time that hand piece assembly 3000 has been activated to the maximum activation period of hand piece assembly 3000 (15050). If the amount of time that hand piece assembly 3000 has been activated is equal to or greater than the maximum activation period of hand piece assembly 3000, system 1000 prevents hand piece assembly 3000 from being enabled (15060). If the amount of time that hand piece assembly 3000 has been activated is less than the maximum activation period of hand piece assembly 3000, system 1000 compares the period of time since hand piece assembly 3000 was activated to the maximum post-use activation period of hand piece assembly 3000 (15070). If the period of time since hand piece assembly 3000 was activated is equal to or greater than the maximum post-activation use period of hand piece assembly 3000, system 1000 prevents hand piece assembly 3000 (2210) from being enabled (15060). If the period of time since hand piece assembly 3000 was first activated is less than the maximum post-activation use period of hand piece assembly 3000, system 1000 enables operation of hand piece assembly 3000 (15080). System 1000 goes through this loop at predetermined time intervals so that, after hand piece assembly 3000 is enabled, hand piece assembly 3000 can be disabled if appropriate. In certain embodiments, the predetermined time interval is at most about five seconds (e.g., at most about four seconds, at most about three seconds, at most about two seconds, at most about one second, at most about 0.5 second, at most about 0.2 second, at most about 0.1 second).

In some embodiments, system 1000 can provide an indication, such as an audio indication (e.g., sounding an alarm) and/or a visual indication (e.g., an LED message on hand piece assembly 3000), to a user a given parameter is approaching a critical value. As an example, system 1000 can provide an indication to a user as acoustic horn assembly 3500 is approaching its maximum use temperature. As an additional example, system 1000 can provide an indication to a user as wire 4000 is approaching its maximum use temperature. As another example, system 1000 can provide an indication to a user as hand piece assembly 3000 is approaching its maximum activation period. As a further example, system 1000 can provide an indication to a user as hand piece assembly 3000 is approaching its maximum post-activation use period. As an additional example, system 1000 can provide an indication to a user as the difference between the vibrational frequency of acoustic horn assembly 3500 and the resonant frequency of acoustic horn assembly 3500 is approaching its maximum value.

While certain embodiments have been described, other embodiments are possible.

As an example, while embodiments have been described in which power switch 3135 is a touch switch, more generally, power switch 3135 can be any switch that can move between a first state (e.g., power supply 2000 on) and a second state (e.g., power supply 2000 off). In some embodiments, power switch 3135 is a slide switch for which displacing the switch to a first position places the switch in the first state and displacing the switch to a second position places the switch in the second state.

As another example, in some embodiments system 1000 can include additional features. In some embodiments, system 1000 can include a catheter that surrounds wire 4000. The catheter can, for example, allow a fluid (e.g., an irrigation fluid, a fluid containing a therapeutic agent, a cooling fluid) to flow between wire 4000 and the catheter, and/or the catheter can assist in steering wire 4000. In embodiments in which system 1000 includes a catheter, system 1000 may include additional equipment to monitor fluid flow through the catheter. For example, system 1000 can include a bubble detector that can detect bubbles in the fluid as it passes through the catheter. The bubble detector can include, for example, an electromagnetic energy emitter (e.g., IR emitter, UV emitter, visible light emitter) and a corresponding detector configured to detect the presence of bubbles in the fluid passing through the catheter. Alternatively or additionally, system 1000 can include a flow meter to regulate the flow rate of fluid through the catheter. Regulation of the flow rate of the fluid can, for example, help to regulate the rate at which wire 4000 is cooled during use. In certain embodiments, one or more portions of system 1000 that will be disposed within a subject during use (e.g., one or more regions of wire 4000) can include a radiopaque material. In certain embodiments, a radiopaque material be disposed at or near the distal end of wire 4000 so that the location of the distal end of wire 4000 can be located within a patient using fluoroscopy. In some embodiments, the radiopaque material can be in the shape of bands disposed on (e.g., painted on, swaged on) wire 4000. In certain embodiments, the radiopaque material can be incorporated into (e.g., alloyed with) the material that forms wire 4000. Examples of radiopaque materials include tungsten, tantalum, rhenium, iridium, silver, gold, bismuth, platinum, molybdenum and alloys thereof. The radiopaque material can, for example, assist in determining the location of wire 4000 within a subject. Examples of the foregoing features are disclosed, for example, in Rabiner et al., U.S. Pat. No. 6,802,835; Rabiner et al. U.S. Pat. No. 6,733,451; and Hare et al., U.S. Pat. No. 6,730,048.

As a further example, while embodiments have been disclosed in which two piezoelectric transducers are used, in certain embodiments a different number (e.g., one, three, four, five, six, seven, eight, nine, 10) of piezoelectric transducers can be used.

As still another example, while the piezoelectric transducers have been described as piezoceramic rings, other types of piezoelectric transducers can be used. Moreover, while embodiments have been disclosed in which piezoelectric transducers are used, other types of transducers may be used. Examples of transducers include magnetostrictive transducers, pneumatic transducers and hydraulic transducers. In some embodiments, combinations of types of transducers can be used.

As an additional example, while embodiments have been described in which wire 4000 is metallurgically bonded with an acoustic coupler, in certain embodiments wire 4000 and the acoustic coupler can be coupled using other techniques. For example, wire 4000 and the acoustic coupler can be coupled with a mechanical connection. In some embodiments, the acoustic coupler is crimped onto wire 4000. For example, the acoustic coupler and wire can be mechanically joined by deforming a cylindrical portion of the coupler around an end region of the wire over a given length. Other mechanical connections are disclosed, for example, in Rabiner et al., U.S. Pat. No. 6,679,873; Ranucci et al., U.S. Pat. No. 6,695,782; and Hare et al., U.S. patent application Ser. No. 2003/0065263.

As another example, while embodiments have been described in which the cross-sectional shape of wire 4000 is circular, other cross-sectional shapes may also be used. For example, the cross-sectional shape of wire 4000 can be triangular, elliptical, or rectangular. In some embodiments, different portions of wire 4000 have different cross-sectional shapes.

As a further example, while embodiments have been disclosed where wire 4000 is formed of Ti-6A1-4V titanium, in certain embodiments, wire 4000 can be formed of a different material. In general, wire 4000 can be formed of any material capable of supporting ultrasonic vibrations. In some embodiments, wire 4000 is formed of a material having a flexural stiffness of at least about $1 \times 10^7$ N/m (e.g., at least about $2.5 \times 10^7$ N/m, at least about $4 \times 10^7$ N/m) and/or at most about $10 \times 10^7$ N/m (e.g., at least about $8.5 \times 10^7$ N/m, at least about $7 \times 10^7$ N/m). Examples of materials from which wire 4000 can be made include metals (e.g., titanium, stainless steel) and alloys (e.g., titanium alloys other than annealed Ti-6A1-4V titanium, stainless steel alloys).

As an additional example, while embodiments of an unbent wire 4000 have been shown, it is to be understood that, in general, during the use of system 1000, wire 4000 will be bent. In some embodiments, during use of system 1000, wire 4000 may have one or more bends. In certain embodiments, when bent, wire 4000 may take on a shape that is helical (along axis 4015). In some embodiments, wire 4000 may bend in multiple planes (e.g., as compared to axis 4015).

As another example, while power supply 2000 has been described as including input device 2006 to allow the user to program or modify certain operational parameters of system 1000, in some embodiments, power supply includes no such input device. In such embodiments, for example, the user can be prevented from programming or modifying any operational parameters of the system.

As yet a further example, while embodiments have been described in which a multi-wire cable provides communication between power supply 2000 and hand piece assembly 3000, other communication devices can be used. In some embodiments, a one-wire cable can provide the communication path between power supply 2000 and hand piece assembly 3000. An exemplary one-wire cable is described in Dallas Semiconductor Data Sheet DS2436 and Dallas Semiconductor Data Sheet DS2480. In certain embodiments, a single wire of the one-wire cable can be used to transmit both power and information between power supply 2000 and hand piece assembly 3000. In some embodiments, a wireless communication system can provide the communication path between power supply 2000 and hand piece assembly 3000 while a wire provides the electrical current path to deliver power from power supply 2000 and hand piece assembly 3000. Combinations of devices are also possible.

As another example, in certain embodiments, hand piece assembly 3000 can be labeled to indicate the procedure for which hand piece assembly 3000 is designed to be used. Exemplary labels include stickers applied to the hand piece assembly 3000 and/or a package which includes the hand piece assembly 3000, a label printed on a package which includes the hand piece assembly 3000, a label printed on the hand piece assembly 3000, an RFID tag included in the hand piece assembly 3000, and an RFID tag included in the package which includes the hand piece assembly 3000. The labels can include various information such as the procedure the hand piece assembly 3000 is designed to be used for, the length of wire 4000, and/or an expiration date for the hand piece assembly 3000. Such labeling can allow for quick and easy selection by a user, and/or can reduce the possibility that improper equipment will be used for a given procedure. In some embodiments, a labeled hand piece assembly can have the appropriate operational parameters stored in its memory so that the ultrasound vibration system operates in appropriate fashion for the given procedure.

As a further example, while embodiments have been described in which hand piece assembly 3000 automatically transfers operational parameters 3016 to power supply 2000 when hand piece assembly 3000 is connected to power supply 2000, other methods for transferring operational parameters 3016 from hand piece assembly 3000 to power supply 2000 are possible. For example, in some embodiments, power supply 2000 detects a connection to hand piece assembly 3000 and power supply 2000 sends a request to hand piece assembly 3000 for operational parameters 3016. Hand piece assembly 3000 receives the request and, in response, sends the requested operational parameters 3016 to power supply 2000.

As an additional example, while embodiments have been described in which memory 3014 stores one or more operational parameters 3016, in some embodiments memory 3014 can store one or more identifiers (e.g., character identifiers including letters and/or numbers) corresponding to a particular operational parameter or a particular set of operational parameters in addition to, or instead of, storing operational parameters. In such embodiments, hand piece assembly 3000 can transfer the identifier(s) to power supply 2000 upon connection of hand piece assembly 3000 to power supply 2000. Power supply 2000 can use the identifier(s), for example, to determine a set of operational parameters for activation and/or operation of system 1000. For example, power supply 2000 can include a database or look-up table of operational parameters and associated identifiers which can be used to determine the correct set of one or more operational parameters based on the identifier(s) received from memory 3014. Storing one or more identifiers in memory 3014 can provide the advantage of reducing the size of the memory in hand piece assembly 3000 compared to the size of a memory used to store multiple operational parameters. As an example, in some embodiments, the identifier(s) can indicate the length of wire 4000, and the identifier(s) can provide appropriate operational parameters for power supply 2000 to operate system 1000 given the length of wire 4000. As another example, in certain embodiments, the identifier(s) can indicate a procedure to be performed with system 1000, and the identifier(s) can provide appropriate operational parameters for power supply 2000 to operate system 1000 given the procedure to be performed.

As another example, while embodiments have been described in which voltage 10060 is divided into five regions, in certain embodiments output voltage 10060 analog control loop 10000 can be divided into fewer regions (e.g., two regions, three regions, four regions) or more regions (e.g., six regions, seven regions, eight regions, nine regions, 10 regions, 11, regions, 12 regions).

As an additional example, while embodiments have been described in which voltage 10070 is divided into six bins, in certain embodiments voltage 10070 can be divided into fewer bins (e.g., two bins, three bins, four bins, five bins) or more regions (e.g., seven bins, eight bins, nine bins, 10 bins, 11, bins, 12 bins).

Figure 26:
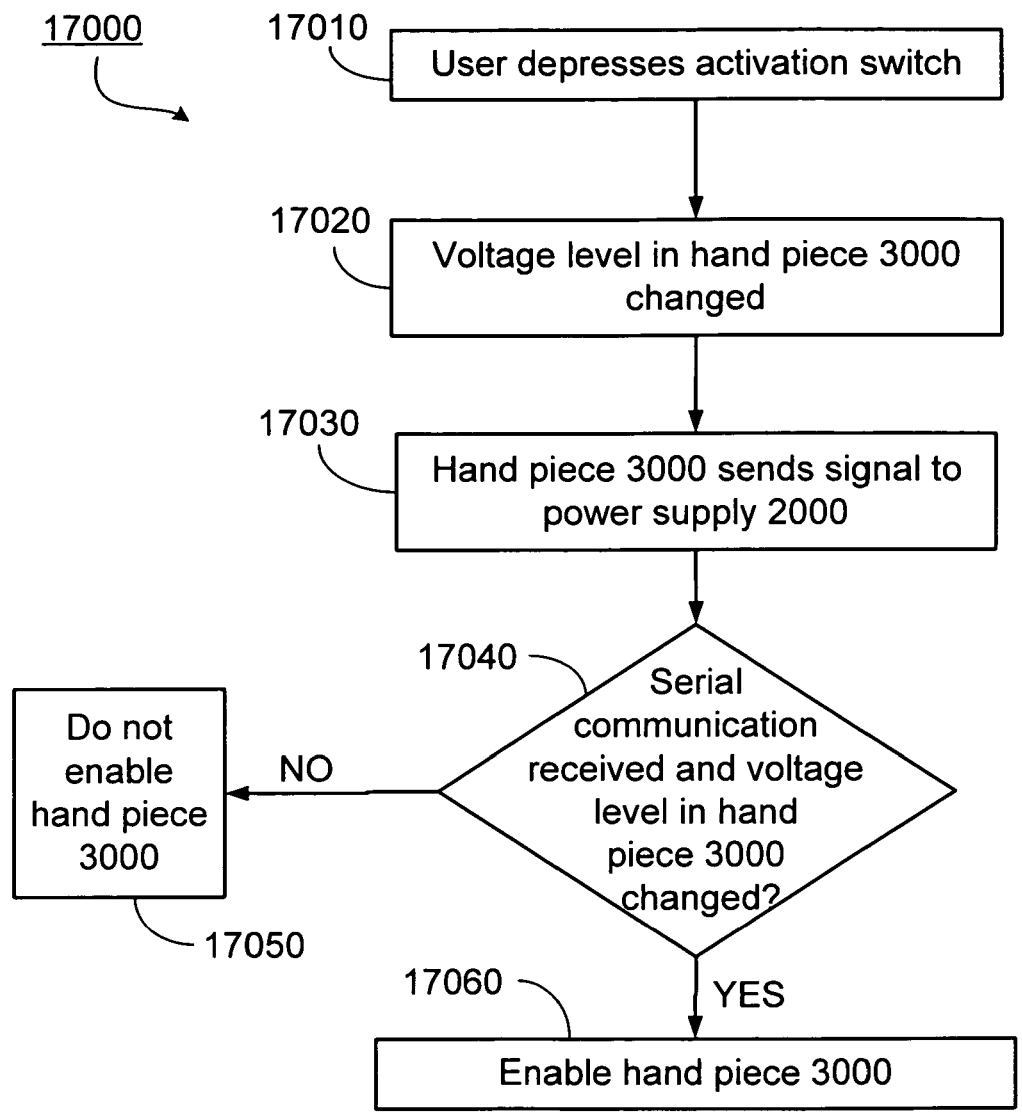
FIG. 26 shows a process for confirming activation of a hand piece assembly.

As a further example, in some embodiments, hand piece assembly 3000 can include an activation switch that an operator of system 1000 can depress to activate hand piece assembly 3000. Examples of activation switches include buttons, touch screens and mechanical switches. In certain embodiments, when the user depresses the activation switch, hand piece assembly 3000 can send a message to power supply 2000 to activate hand piece assembly 3000. Optionally, system 1000 can be designed to include appropriate circuitry to confirm that the user has actually depressed the activation switch before activating hand piece assembly 3000 (e.g., to confirm that the signal received by power supply 2000 was not an error). FIG. 26 shows a process 17000 for confirming that an activation switch has been pressed prior to activating hand piece assembly 3000. In order to activate hand piece assembly 3000, an operator presses the activation switch (17010). In response, a voltage level on hand piece assembly 3000 is changed (17020). For example, a voltage level in hand piece assembly 3000 can be changed from a system high voltage level to a system low voltage level (e.g., from 8 V to 3.5 V, from 5 V to 0 V). Hand piece assembly 3000 also sends a serial communication to power supply 2000 over communication line 2012 in response to activation switch being pressed (17030). Power supply 2000 determines if both the serial communication has been received and the voltage level in hand piece assembly 3000 has dropped (17040). If both the serial communication has been received and the voltage level in hand piece assembly 3000 has dropped, hand piece assembly 3000 is enabled (17050). Otherwise, hand piece assembly 3000 remains disabled (17040).

While certain embodiments discussed above describe acoustic horn assembly 3500 and wire 4000 as being designed to vibrate longitudinally, other designs are possible. For example, acoustic horn assembly 3500 and/or wire 4000 can be designed to vibrate longitudinally, transversely, and/or torsionally.

Other embodiments are in the claims.

What is claimed is:

1. A method, comprising:
   determining an absolute value of a first input to a voltage controlled oscillator (VCO) that is in electrical communication with an acoustic assembly of an ultrasound medical device; and
   if the absolute value of the first input to the VCO is in a first range, maintaining a second input to the VCO, the first range comprising zero and nonzero values;
   if the absolute value of the first input to the VCO is in a second range, adjusting the second input to the VCO by a first voltage; and
   if the absolute value of the first input to the VCO is in a third range, adjusting the second input to the VCO by a second voltage,
      wherein an absolute value of the second voltage is greater than an absolute value of the first voltage, and
      wherein a maximum value of the first range is less than a minimum value of the second range, and a maximum value of the second range is less than a minimum value of the third range.

2. The method of claim 1, wherein the second voltage is at least about 5% greater than the first voltage.

3. The method of claim 1, wherein the first voltage is configured to generate a change in an output frequency of a voltage generated by the VCO having an absolute value of at least about 20 Hz.

4. The method of claim 1, wherein the second voltage is configured to generate a change in an output frequency of the VCO of at least about 40 Hz.

5. The method of claim 1, wherein the acoustic assembly has a resonant frequency, and the method further comprises adjusting the first input to the VCO based on a change in the resonant frequency of the acoustic assembly.

6. The method of claim 5, wherein the resonant frequency comprises a harmonic of a fundamental resonant frequency of the acoustic assembly.

7. The method of claim 1, wherein the acoustic assembly has a resonant frequency, and the method further comprises determining the resonant frequency of the acoustic assembly.

8. The method of claim 1, wherein the ultrasound medical device comprises an ultrasound vibration device, the ultrasound vibration device comprising the acoustic assembly and an ultrasonic probe.

9. One or more computer-readable media storing instructions that are executable on one or more processing devices, the instructions for causing the one or more processing devices to:
   determine an absolute value of an error input to a voltage controlled oscillator (VCO) that is in electrical communication with an acoustic assembly of an ultrasound medical device; and
   if the absolute value of the first input to the VCO is in a first range, maintain a second input to the VCO, the first range comprising zero and nonzero values;
   if the absolute value of the first input to the VCO is in a second range, adjust the second input to the VCO by a first voltage; and
   if the absolute value of the first input to the VCO is in a third range, adjust the second input to the VCO by a second voltage,
      wherein an absolute value of the second voltage is greater than an absolute value of the first voltage, and
      wherein a maximum value of the first range is less than a minimum value of the second range, and a maximum value of the second range is less than a minimum value of the third range.

10. The one or more computer-readable media of claim 9, wherein the first voltage is configured to generate a change in an output frequency of a voltage generated by the VCO having an absolute value of at least about 20 Hz.

11. The one or more computer-readable media of claim 9, wherein the second voltage is configured to generate a change in an output frequency of the VCO of at least about 40 Hz.

12. The one or more computer-readable media of claim 9, further comprising instructions to cause a machine to adjust the first input based on a change in a resonant frequency of the acoustic assembly.

13. The one or more computer-readable media of claim 12, wherein the resonant frequency comprises a harmonic of a fundamental resonant frequency of the acoustic assembly.

14. The one or more computer-readable media of claim 9, further comprising instructions to cause a machine to determine a resonant frequency of the acoustic assembly.

15. An ultrasound medical system, comprising:
   an ultrasound medical device comprising an ultrasound vibration device, the ultrasound vibration device comprising an acoustic assembly;
   a voltage controlled oscillator (VCO) in electrical communication with the ultrasound vibration device; and
   a control unit configured to:
      determine an absolute value of an error input to the VCO that is in electrical communication with the ultrasound vibration device; and
      if the absolute value of the first input to the VCO is in a first range, maintain a second input to the VCO, the first range comprising zero and nonzero values;
      if the absolute value of the first input to the VCO is in a second range, adjust the second input to the VCO by a first voltage; and
      if the absolute value of the first input to the VCO is in a third range, adjust the second input to the VCO by a second voltage,
         wherein an absolute value of the second voltage is greater than an absolute value of the first voltage, and wherein a maximum value of the first range is less than a minimum value of the second range, and a maximum value of the second range is less than a minimum value of the third range.

16. The system of claim 15, wherein the ultrasound vibration device comprises an ultrasonic probe.

17. The system of claim 15, wherein the control unit is further configured to adjust the first input based on a change in a resonant frequency of the acoustic assembly.

18. The system of claim 17, wherein the resonant frequency comprises a harmonic of a fundamental resonant frequency of the acoustic assembly.

19. The system of claim 15, wherein the acoustic assembly is in electrical communication with the VCO.

20. The system of claim 19, wherein the ultrasound vibration device further comprises a wire coupled to the acoustic assembly.

* * * * *